US009671403B2

(12) United States Patent
Heyduk et al.

(10) Patent No.: US 9,671,403 B2

(45) Date of Patent: *Jun. 6, 2017

(54) BIOSENSOR FOR DETECTING MULTIPLE EPITOPES ON A TARGET

(71) Applicants: Saint Louis University, St. Louis, MO (US); Mediomics LLC, St. Louis, MO (US)

(72) Inventors: Tomasz Heyduk, Ballwin, MO (US); Ling Tian, St. Louis, MO (US)

(73) Assignees: MEDIOMICS, LLC, St. Louis, MO (US); SAINT LOUIS UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/673,336

(22) Filed: Mar. 30, 2015

(65) Prior Publication Data

US 2015/0226739 A1 Aug. 13, 2015

Related U.S. Application Data

(63) Continuation of application No. 13/133,198, filed as application No. PCT/US2009/065142 on Nov. 19, 2009, now Pat. No. 8,993,245.

(60) Provisional application No. 61/116,875, filed on Nov. 21, 2008.

(51) Int. Cl.

| | |
|---|---|
| ***G01N 33/53*** | (2006.01) |
| ***C12Q 1/68*** | (2006.01) |
| ***C07H 21/02*** | (2006.01) |
| ***C40B 30/04*** | (2006.01) |
| ***G01N 31/22*** | (2006.01) |
| ***G01N 33/566*** | (2006.01) |
| ***G01N 33/569*** | (2006.01) |
| ***G01N 33/542*** | (2006.01) |

(52) U.S. Cl.

CPC ..... *G01N 33/56916* (2013.01); *G01N 33/542* (2013.01); *G01N 2333/245* (2013.01); *G01N 2333/255* (2013.01)

(58) Field of Classification Search

CPC .......... C12Q 1/68; C12M 1/34; G01N 33/542

USPC ....... 435/6.1, 7.1; 536/23.1; 506/9; 422/400; 436/501

See application file for complete search history.

(56) References Cited

U.S. PATENT DOCUMENTS

| | | | |
|---|---|---|---|
| 4,894,347 | A | 1/1990 | Hillyard et al. |
| 5,270,163 | A | 12/1993 | Gold et al. |
| 5,475,096 | A | 12/1995 | Gold et al. |
| 5,476,766 | A | 12/1995 | Gold et al. |
| 5,543,293 | A | 8/1996 | Gold et al. |
| 5,567,588 | A | 10/1996 | Gold et al. |
| 5,582,981 | A | 12/1996 | Toole et al. |
| 5,637,459 | A | 6/1997 | Burke et al. |
| 5,641,629 | A | 6/1997 | Pitner et al. |
| 5,650,275 | A | 7/1997 | Pitner et al. |
| 5,660,985 | A | 8/1997 | Pieken et al. |
| 5,670,637 | A | 9/1997 | Gold et al. |
| 5,683,867 | A | 11/1997 | Biesecker et al. |
| 5,688,935 | A | 11/1997 | Stephens et al. |
| 5,696,249 | A | 12/1997 | Gold et al. |
| 5,705,337 | A | 1/1998 | Gold et al. |
| 5,712,375 | A | 1/1998 | Jensen et al. |
| 5,723,289 | A | 3/1998 | Eaton et al. |
| 5,723,592 | A | 3/1998 | Eaton et al. |
| 5,750,342 | A | 5/1998 | Stephens et al. |
| 5,756,291 | A | 5/1998 | Griffin et al. |
| 5,763,566 | A | 6/1998 | Jensen et al. |
| 5,763,595 | A | 6/1998 | Gold et al. |
| 5,773,598 | A | 6/1998 | Burke et al. |
| 5,789,157 | A | 8/1998 | Jensen et al. |
| 5,789,160 | A | 8/1998 | Eaton et al. |
| 5,817,785 | A | 10/1998 | Gold et al. |
| 5,840,867 | A | 11/1998 | Toole et al. |
| 5,843,653 | A | 12/1998 | Gold et al. |
| 5,853,984 | A | 12/1998 | Davis et al. |
| 5,858,660 | A | 1/1999 | Eaton et al. |
| 5,861,254 | A | 1/1999 | Schneider et al. |
| 5,864,026 | A | 1/1999 | Jensen et al. |
| 5,874,218 | A | 2/1999 | Drolet et al. |
| 5,958,691 | A | 9/1999 | Pieken et al. |
| 5,962,219 | A | 10/1999 | Gold et al. |
| 5,989,823 | A | 11/1999 | Jayasena et al. |
| 5,998,142 | A | 12/1999 | Gold et al. |
| 6,001,570 | A | 12/1999 | Grossman |
| 6,001,577 | A | 12/1999 | Gold et al. |
| 6,011,020 | A | 1/2000 | Gold et al. |
| 6,013,443 | A | 1/2000 | Heilig et al. |
| 6,024,918 | A | 2/2000 | Hendriks et al. |
| 6,030,776 | A | 2/2000 | Eaton et al. |
| 6,048,698 | A | 4/2000 | Eaton et al. |

(Continued)

FOREIGN PATENT DOCUMENTS

| | | | |
|---|---|---|---|
| JP | 2003508729 | A1 | 3/2003 |
| WO | 9700446 | A1 | 1/1997 |

(Continued)

OTHER PUBLICATIONS

Darmanis et al., "Self-assembly of proximity probes for flexible and modular proximity ligation assays", BioTechniques, 2007, pp. 443-450, vol. 43, No. 4.

(Continued)

*Primary Examiner* — Narayan Bhat

(74) *Attorney, Agent, or Firm* — Polsinelli PC

(57) ABSTRACT

The present invention encompasses a method for detecting a target comprising a repeating epitope.

7 Claims, 18 Drawing Sheets

(17 of 18 Drawing Sheet(s) Filed in Color)

(56) References Cited

U.S. PATENT DOCUMENTS

| | | | |
|---|---|---|---|
| 6,083,696 | A | 7/2000 | Biesecker et al. |
| 6,110,900 | A | 8/2000 | Gold et al. |
| 6,114,120 | A | 9/2000 | Jensen et al. |
| 6,127,119 | A | 10/2000 | Stephens et al. |
| 6,147,204 | A | 11/2000 | Gold et al. |
| 6,177,555 | B1 | 1/2001 | Jayasena et al. |
| 6,207,388 | B1 | 3/2001 | Grossman |
| 6,225,058 | B1 | 5/2001 | Munishkin et al. |
| 6,261,774 | B1 | 7/2001 | Pagratis et al. |
| 6,261,783 | B1 | 7/2001 | Jayasena et al. |
| 6,287,772 | B1 | 9/2001 | Stefano et al. |
| 6,291,184 | B1 | 9/2001 | Gold et al. |
| 6,300,074 | B1 | 10/2001 | Gold et al. |
| 6,329,145 | B1 | 12/2001 | Janjic et al. |
| 6,331,398 | B1 | 12/2001 | Gold et al. |
| 6,344,318 | B1 | 2/2002 | Gold et al. |
| 6,376,190 | B1 | 4/2002 | Gold et al. |
| 6,380,377 | B1 | 4/2002 | Dattagupta et al. |
| 6,391,593 | B1 | 5/2002 | Weston et al. |
| 6,399,302 | B1 | 6/2002 | Lannigan et al. |
| 6,423,493 | B1 | 7/2002 | Gorenstein et al. |
| 6,451,588 | B1 | 9/2002 | Egholm et al. |
| 6,465,188 | B1 | 10/2002 | Gold et al. |
| 6,506,887 | B1 | 1/2003 | Smith et al. |
| 6,511,809 | B2 | 1/2003 | Baez et al. |
| 6,544,746 | B2 | 4/2003 | Heyduk |
| 6,566,495 | B1 | 5/2003 | Fodor et al. |
| 6,593,091 | B2 | 7/2003 | Keys et al. |
| 6,613,526 | B2 | 9/2003 | Heilig et al. |
| 6,680,377 | B1 | 1/2004 | Stanton et al. |
| 6,716,583 | B2 | 4/2004 | Gold et al. |
| 6,730,482 | B2 | 5/2004 | Gold et al. |
| 6,815,164 | B2 | 11/2004 | Kurn |
| 6,878,515 | B1 | 4/2005 | Landegren |
| 6,916,613 | B2 | 7/2005 | Munishkin et al. |
| 7,125,660 | B2 | 10/2006 | Stanton et al. |
| 7,172,865 | B2 | 2/2007 | Heyduk et al. |
| 7,282,328 | B2 | 10/2007 | Kong et al. |
| 7,306,904 | B2 | 12/2007 | Landegren et al. |
| 7,419,835 | B2 | 9/2008 | Torres et al. |
| 7,435,542 | B2 | 10/2008 | Shi et al. |
| 7,576,192 | B2 | 8/2009 | Heyduk |
| 7,795,009 | B2 | 9/2010 | Heyduk |
| 7,811,809 | B2 | 10/2010 | Heyduk et al. |
| 7,939,313 | B2 | 5/2011 | Heyduk et al. |
| 8,431,388 | B2 | 4/2013 | Heyduk |
| 8,592,202 | B2 | 11/2013 | Heyduk et al. |
| 8,945,840 | B2 | 2/2015 | Heyduk et al. |
| 8,956,857 | B2 | 2/2015 | Heyduk et al. |
| 8,993,245 | B2 | 3/2015 | Heyduk et al. |
| 9,040,287 | B2 | 5/2015 | Chang et al. |
| 2002/0022224 | A1 | 2/2002 | Hornby et al. |
| 2002/0037506 | A1 | 3/2002 | Lin et al. |
| 2002/0051986 | A1 | 5/2002 | Baez et al. |
| 2002/0064779 | A1 | 5/2002 | Landegren et al. |
| 2003/0087239 | A1 | 5/2003 | Stanton et al. |
| 2003/0207271 | A1 | 11/2003 | Holwitt et al. |
| 2003/0224435 | A1 | 12/2003 | Seiwert |
| 2003/0232383 | A1 | 12/2003 | Daunert et al. |
| 2003/0232388 | A1 | 12/2003 | Kreimer et al. |
| 2004/0053310 | A1 | 3/2004 | Shi et al. |
| 2004/0058378 | A1 | 3/2004 | Kong et al. |
| 2004/0067501 | A1 | 4/2004 | Kage |
| 2004/0180360 | A1 | 9/2004 | Wilson et al. |
| 2004/0219523 | A1 | 11/2004 | Stanton et al. |
| 2005/0009050 | A1 | 1/2005 | Nadeau et al. |
| 2005/0069910 | A1 | 3/2005 | Turner et al. |
| 2005/0089890 | A1 | 4/2005 | Cubicciotti |
| 2005/0095627 | A1 | 5/2005 | Kolman et al. |
| 2005/0106594 | A1 | 5/2005 | Ellington et al. |
| 2005/0112710 | A1 | 5/2005 | Torres et al. |
| 2005/0221408 | A1 | 10/2005 | Nalefski et al. |
| 2006/0110739 | A1 | 5/2006 | Heyduk |
| 2007/0154899 | A1 | 7/2007 | Coull et al. |
| 2007/0287197 | A1 | 12/2007 | Harris et al. |
| 2008/0044826 | A1 | 2/2008 | Heyduk |
| 2008/0044834 | A1 | 2/2008 | Heyduk et al. |
| 2008/0171322 | A1 | 7/2008 | Heyduk et al. |
| 2009/0202990 | A1 | 8/2009 | Heyduk et al. |
| 2010/0021899 | A1 | 1/2010 | Ikebukuro et al. |
| 2010/0297654 | A1 | 11/2010 | Heyduk |
| 2011/0091893 | A1 | 4/2011 | Heyduk et al. |
| 2012/0028242 | A1 | 2/2012 | Heyduk et al. |
| 2013/0034846 | A1 | 2/2013 | Chang et al. |
| 2014/0243208 | A1 | 8/2014 | Chang et al. |
| 2014/0248710 | A1 | 9/2014 | Heyduk et al. |
| 2015/0191779 | A1 | 7/2015 | Heyduk et al. |
| 2015/0219668 | A1 | 8/2015 | Heyduk et al. |
| 2015/0253315 | A1 | 9/2015 | Chang et al. |
| 2016/0077088 | A1 | 3/2016 | Chang et al. |

FOREIGN PATENT DOCUMENTS

| | | | |
|---|---|---|---|
| WO | 0070329 | A1 | 11/2000 |
| WO | 03064657 | A1 | 8/2003 |
| WO | 03078449 | A2 | 9/2003 |
| WO | 2005059509 | A2 | 6/2005 |
| WO | 2006128138 | A2 | 11/2006 |
| WO | 2006135527 | A2 | 12/2006 |
| WO | 2007005649 | A2 | 1/2007 |
| WO | 2008108873 | A2 | 9/2008 |
| WO | 2010059820 | A1 | 5/2010 |
| WO | 2011/100561 | A1 | 8/2011 |
| WO | 2013016280 | A2 | 1/2013 |
| WO | 2016/040830 | A1 | 3/2016 |

OTHER PUBLICATIONS

Heyduk, "Practical biophysics: Sensors for rapid detection of biological targets utilizing target-induced oligonucleotide annealing", Biophysical Chemistry, 2010, pp. 91-95, vol. 151.

International Search Report and Written Opinion from related International Patent Application No. PCT/US2011/024547, dated Jun. 28, 2011; 10 pgs.

International Search Report and Written Opinion from related International Patent Application No. PCT/US2015/049733, dated Jan. 29, 2016; 15 pgs.

Notice of Allowance from related U.S. Appl. No. 13/133,198, dated Aug. 28, 2014; 13 pgs.

Notice of Allowance from related U.S. Appl. No. 11/916,776, dated Sep. 19, 2014; 16 pgs.

Notice of Allowance from related U.S. Appl. No. 13/728,226, dated Oct. 1, 2014; 8 pgs.

Notice of Allowance from related U.S. Appl. No. 13/133,198, dated Nov. 18, 2014; 15 pgs.

Notice of Allowance from related U.S. Appl. No. 13/578,718, dated Jan. 27, 2015; 13 pgs.

Supplemental Notice of Allowability from related U.S. Appl. No. 13/578,718, dated Mar. 5, 2015; 4 pgs.

Notice of Allowance from related Canadian Patent Application No. 2,660,129, dated Feb. 10, 2015; 1 page.

Office Action from related European Patent Application No. 03703998.9, dated Jan. 8, 2015; 3 pgs.

Office Action from related European Patent Application No. 03703998.9, dated May 30, 2012; 3 pgs.

Office Action from related Chinese Patent Application No. 201280038577.0, dated Jul. 7, 2015; 14 pgs.

Office Action from related Chinese Patent Application No. 201280038577.0, dated Nov. 3, 2014; 12 pgs.

Office Action from related Canadian Patent Application No. 2,787,483, dated Mar. 19, 2015; 4 pgs.

Office Action from related U.S. Appl. No. 11/609,628, dated Oct. 1, 2008; 5 pgs.

Office Action from related U.S. Appl. No. 13/133,198, dated Nov. 5, 2012; 12 pgs.

Office Action from related U.S. Appl. No. 13/133,198, dated Jun. 27, 2013; 14 pgs.

Office Action from related European Patent Application No. 11742872.2, dated May 19, 2014; 3 pgs.

(56) References Cited

OTHER PUBLICATIONS

Office Action from related European Patent Application No. 11742872.2, dated Apr. 2, 2015; 4 pgs.
Office Action from related U.S. Appl. No. 14/234,329, dated Aug. 7, 2015; 10 pgs.
Office Action from related U.S. Appl. No. 13/578,718, dated Nov. 5, 2014; 21 pgs.
Office Action from related European Patent Application No. 13194822.6, dated Dec. 19, 2014; 4 pgs.
Office Action from related U.S. Appl. No. 14/234,329, dated Apr. 1, 2016; 10 pgs.
Office Action from related U.S. Appl. No. 14/623,348, dated Jun. 17, 2016; 21 pgs.
Stoltenburg et al., "SELEX—A (r)evolutionary method to generate high-affinity nucleic acid ligands", Biomolecular Engineering, 2007, pp. 381-403, vol. 24, No. 4.
Supplementary European Search Report from related European Patent Application No. 12817830.8, dated Nov. 25, 2014; 11 pgs.
Office Action dated Jul. 10, 2012 for related Chinese Patent Application No. 200780037379.1; 7 pages ( with 1 page English translation).
Ozawa et al., "Identification and Characterization of Peptides Binding to Newcastle Disease Virus by Phage Display," J. Vet. Med. Sci., 2005, vol. 67, No. 12, pp. 1237-1241.
Office Action dated Nov. 20, 2012 for related Canadian Patent Application No. 2,611,198, 3 pages.
Request for Postponement of Oral Proceedings dated Jan. 27, 2014 from related European Patent Application No. 04813618.8, 1 page.
Response to Communication Under Article 15 (1) of the Rules of Procedure of the Board of Appeals dated Aug. 1, 2014 from related European Patent Application No. 04813618.8, 8 pages.
Ratilainen et al., "Hybridization of Peptide Nucleic Acid," Biochemistry, 1998, vol. 37, pp. 12331-12342.
Result of Telephone Consultation with Examiner dated Apr. 13, 2010 from related European Patent Application No. 04813618.8, 3 pages.
Roberts et al., "RNA-peptide fusions for the in vitro selection of peptides and proteins," PNAS, Nov. 11, 1997, vol. 94, No. 23, pp. 12297-12302.
Summons to Oral Proceedings dated Dec. 19, 2013 from related European Patent Application No. 04813618.8, 2 pages.
Santalucia et al., "Improved Nearest-Neighbor Parameters for Prediciting DNA Duplex Stability," 1996, Biochemistry, vol. 35, No. 11, pp. 3555-3562.
Santalucia, "A unified view of polymer, dumbbell, and oligonucleotide DNA nearest-neighbor thermodynamics," ONAS, 1998, vol. 95, pp. 1460-1465.
Sayer et al., "Structural characterization of 2'F-RNA aptamer that binds a HIV-1 SU glycoprotein, g120," Biochem. and Biophysic. Res. Comm., 2002, vol. 293, pp. 924-931.
Selvin et al., "Luminescence energy transfer using a terbium chelate: Improvements on fluorescence energy transfer," Proc. Natl. Acad. Sci. USA, Oct. 1994, vol. 91, pp. 10024-10028.
Selvin et al., "Luminescence Resonance Energy Transfer," J. Am. Chem. Soc. 1994, vol. 116, pp. 6029-6030.
Sen et al., "On the stability of peptide nucleic acid duplexes in the presence of organic solvents," Nucleic Acids Research, May 3, 2007, vol. 35, No. 10, pp. 3367-3374.
Sequence alignment brochure SEQ ID No. 1 and 2, http://blast.ncbi.nim.nih.gov/Blast.cgi, printed Sep. 13, 2009, 1 page.
Sequence alignment brochure SEQ ID No. 1 and 3, http://blast.ncbi.nim.nih.gov/Blast.cgi, printed Sep. 13, 2009, 1 page.
Sequence alignment brochure SEQ ID No. 2 and 3, http://blast.ncbi.nim.nih.gov/Blast.cgi, printed Sep. 13, 2009, 1 page.
Sequence alignment brochure SEQ ID No. 5 and 12, http://blast.ncbi.nim.nih.gov/Blast.cgi, printed Sep. 13, 2009, 1 page.
Sequence alignment brochure SEQ ID No. 7 and 12, http://blast.ncbi.nim.nih.gov/Blast.cgi, printed Sep. 13, 2009, 1 page.
Statement of Grounds for Appeal dated Oct. 15, 2010 from related European Patent Application No. 04813618.8, 22 pages.
Supplementary European Search Report dated Jun. 11, 2010 from related European Patent Application No. 06770407.2, 1 page.
Tanaka et al., "Specificity of Hybridization between DNA Sequences based on Free Energy," DNA Computing, Springer-Verlag Berlin Heidelberg, 2006 pp. 371-379.
Tasset et al., "Oligonucleotide Inhibitors of Human Thrombin that Bind Distinct Epitopes," J. Mol. Biol., 1997, vol. 272, No. 5, pp. 688-698.
Telephone Consultation Records faxed May 6, 2010 regarding telephone interviews held on Apr. 27 and May 3, 2010 for related European Patent Application No. 04813618.8, 5 pages.
Turek et al., "Systematic Evolution of Ligands by Exponential Enrichment: RNA Ligands to Bacteriophage T4 DNA Polymerase," Science, 1990, vol. 249, No. 4968, pp. 505-510.
Rockett et al., "DNA arrays: technology, options and toxicological applications," Xenobiotica, 2000, vol. 30, No. 2, pp. 155-177.
Uptima FT-UP17412 SMCC sSMCC Heterobifunctional cross-linkers brochure, undated (no date was provided by Examiner), 3 pages, in Office Action dated Jul. 2, 2008 in related U.S. Appl. No. 10/539,107.
Uptima FT-UP79042 SPDP, Ic-Spdp, Sulfo-Ic-SPDP Heterobifunctional cross-linkers brochure, undated (date provided by Examiner was Sep. 15, 2009), 3 pages, in Office Action dated Sep. 30, 2009 in related U.S. Appl. No. 11/836,333.
Wilson et al., "In Vitro Selection of Functional Nucleic Acids," Ann. Rev. Biochem. 1999, vol. 68, pp. 611-647.
Written Submissions dated Apr. 22, 2010 from related European Patent Application No. 04813618.8, 15 pages.
Written Submissions dated Apr. 30, 2010 from related European Patent Application No. 04813618.8, 37 pages.
Written Submission dated Apr. 6, 2010 from related European Patent Application No. 04813618.8, 16 pages.
Xu et al., "Anti-peptide aptamers recognize amino acid sequence and bind a protein epitope," Proc. Natl. Acad. Sci., 1996, vol. 93, pp. 7475-7480.
Yamamoto et al., "Molecular beacon aptamer fluoresces in the presence of Tat protein of HIV-1," Genes Cells, 2000, vol. 5, pp. 389-396.
Zalipsky, "Chemistry of polyethylene glycol conjugates with biologically active molecules," Advanced Drug Delivery Reviews, 1995, vol. 16, pp. 157-182.
Zhang et al., "A Simple Statistical Parameter for Use in Evaluation and Validation of High Throughput Screening Assays," J. Biomol. Screenings, Nov. 2, 1999, vol. 4, No. 2, pp. 67-73.
Abravaya et al., "Detection of point mutations with a modified ligase chain reaction (Gap-LCR)," Nucleic Acids Research, 1995, pp. 675-682, vol. 23, No. 4.
Bevan et al., "Sequencing of PCR-amplified DNA," PCR Methods and Applications, Genome Research, 1992, vol. 1, pp. 222-228.
Bock et al., "Selection of single-stranded DNA molecules that bind and inhibit human thrombin," Nature, 1992, vol. 355, pp. 564-566.
Burgstaller et al., "Synthetic Ribozymes and the First Deoxyribozyme," Angew. Chem. Int. Ed. English, 1995, vol. 34, No. 11, pp. 1189-1192.
Boder et al., "Yeast surface display for screening combinatorial polypeptide libraries," Nat. Biotech., 1997, vol. 15, pp. 553-557.
Chemical bond, http://en.wikipedia.org/wiki/Chemical_bond, printed Jun. 24, 2008, 11 pages.
Daniels et al., "Generation of RNA Aptamers to the G-Protein-Coupled Receptor for Neurotensin, NTS-1," Analytical Biochemistry, 2002, vol. 305, pp. 214-226.
Decision of Refusal dated Aug. 23, 2011 from related Japanese Patent Application No. 2006-543991, 3 pages with 3 pages English Translation.
Decision on Oral Proceedings dated May 26, 2010 from related European Patent Application No. 04813618.8, 7 pages.
Decision to Grant dated Nov. 14, 2011 from related European Patent Application No. 06770407.2, 5 pages.
Decision to Grant dated Sep. 5, 2013 from related European Patent Application No. 07873908.3, 2 pages.
Ellington et al., "In vitro selection of RNA molecules that bind specific ligands," Nature, 1990, vol. 346, pp. 818-822.

(56) References Cited

OTHER PUBLICATIONS

Extended European Search Report dated Dec. 22, 2009 for related European Patent Application No. 07873908.3, 6 pages.
European Supplementary Search Report dated Apr. 23, 2008 from related European Patent Application No. 04813618.8, 2 pages.
Extended European Search Report dated Jul. 9, 2010 from related European Patent Application No. 06770407.2, 4 pages.
Extended European Search Report dated Jan. 17, 2014 from related European Patent Application No. 13194822.6, 6 pages
Extended European Search Report dated Aug. 23, 2013 from related European Patent Application No. 11742872.2, 6 pages.
Famulok et al., "Selection of Functional RNA and DNA Molecules from Randomized Sequences," Nucl. Acids. and Mol. Biol., vol. 7.
Famulok et al., "In Vitro Selection of Specific Ligand-binding Nucleic Acids," Angew. Chem. Int. Ed. Engl., 1992, vol. 31, pp. 979-988.
Fang et al., "Synthetic Aptamers to Detect Protein Molecular Variants in a High-Throughput Fluorescence Quencing Assay," ChemBioChem., 2003, vol. 4, pp. 829-834.
Fredriksson et al., "Protein Detection Using Proximity-dependent DNA Ligation Assays," Nature Biotechnology, 2002, vol. 20, pp. 473-477.
Gold et al., "Diversity of Oligonucleotide Functions," Ann. Rev. Biochem., 1995, vol. 64, pp. 763-797.
Heyduk et al., "Fluorescent homogenous immunosensors for detecting pathogenic bacteria," Anal. Biochem., 2010, vol. 396, No. 2, pp. 298-303.
Hamaguchi et al., "Aptamer Beacons for the Direct Detection of Proteins," Analyt. Biochem., 2001, vol. 294, pp. 126-131.
Heyduk, "Nucleic Acid-Based Fluorescence Sensors for Detecting Proteins," Analytical Chemistry, 2005, vol. 77, No. 1, pp. 1147-1156.
Heyduk et al., "Conformational Changes of DNA Induced by Binding of Chironomus High Mobility Group Protein 1a (cHMG1a)," J. Biol. Chem., 1997, vol. 272, No. 32, pp. 19763-19770.
Heyduk et al., "Homogeneous Fluorescence Assay for Cyclic AMP," Comb. Chem. and High Throughput Screen, 2003, vol. 6, pp. 347-354.
Heyduk et al., "Molecular beacons for detecting DNA binding proteins: mechanism of action," Analyt. Biochem, 2003, vol. 316, pp. 1-10.
Heyduk et al., "Thiol-reactive, Luminescent Europium Chelates Luminescence Probes for Resonance Energy Transfer Distance Measurements in Biomolecules," Anal. Biochem, 1997, vol. 248, pp. 216-227.
Heyduk et al., "Luminescense Energy Transfer with Lanthanide Chelates: Interpretation of Sensitized Acceptor Decay Amplitutes," Analyt. Biochem, 2001, vol. 289, No. 1, pp. 60-67.
Heyduk et al., "Molecular beacons for detecting DNA binding proteins," Nat. Biotech., 2002, vol. 20 pp. 171-176.
HyTher-Hibridization Thermodynamics-Module 1', http://ozone3.chem.wayne.edu/cgi-bin/login/execs/HytherMI.cgi, printed Mar. 5, 2009, 1 page.
International Search Report and Written Opinion dated Aug. 25, 2008 for related International Patent Application No. PCT/US2007/075560; 10 pages.
International Search Report and Written Opinion dated Aug. 3, 2007 for related International Patent Application No. PCT/US2006/018845; 8 pages.
International Search Report and Written Opinion dated Jan. 20, 2010 for related International Patent Application No. PCT/US2009/065142; 7 pages.
International Search Report and Written Opinion dated Sep. 24, 2007 for related International Patent Application No. PCT/US2004/041315; 6 pages.
International Search Report and Written Opinion dated Jan. 11, 2013 for related International Patent Application No. PCT/US12/47840; 19 pages.
Jeppesen et al., "Impact of Polymer Tether Length on Mutiple Ligand-Receptor Bond Formation," 2011, vol. 293, pp. 465-468.
Jayasena, "Aptamers: An Emerging Class of Molecules that Rival Antibodies in Diagnostics," Clin. J. Chem, 1999, vol. 45, No. 9, pp. 1628-1650.
Klug et al., "All you wanted to know about SELEX (but were afraid to ask . . . )," Mol. Biol. Rep. 1994, vol. 20, pp. 7-107.
Knoll et al., "Unimolecular Beacons for the Detection of DNA-Binding Proteins," Anal. Chem. 2004, vol. 76, No. 4, pp. 1156-1164.
Keefe et al., "Functional proteins from a random-sequence library," Nature, 2001, vol. 410, pp. 715-718.
Lipovsek et al., "In-vitro protein evolution by ribosome display and mRNA display," J. Imm. Methods, 2004, vol. 290, pp. 51-67.
Li et al., "Molecular Aptamer Beacons for Real-Time Protein Recognition," Biochem, and Biophys. Res. Commun., 2002, vol. 292, No. 1, pp. 31-40.
Mathis, "Probing Molecular Interactions with Homogeneous Techniques Based on Rare Earth Cryptrates and Fluorescence Energy Transfer," Clininc Chem, 1995, vol. 41, No. 9, pp. 1391-1397.
Matlock et al., "Sequence Determinants for the Recognition of the Fork Junction DNA Containing the -10 Region of Promoter DNA by *E. coli* RNA Polymerase," Biochem., 2000, vol. 39, No. 40, pp. 12274-12283.
Mills et al., "Flexibility of Single-Stranded DNA: Use of Gapped Duplex Helices to Determine the Persistence Lengths of Poly (dT) and Poly (dA)," J. Mol., Biol. 1999, vol. 285, pp. 245-257.
Minutes of Oral Proceedings dated May 20, 2010 from related European Patent Application No. 04813618.8, 5 pages.
Notice of Allowance dated Feb. 29, 2012 from related Chinese Patent Application No. 200480036874.7, 3 pages.
Notice of Allowance dated Jul. 24, 2013 from related U.S. Appl. No. 12/961,135, 27 pages.
Francisco et al., "Production and fluorescence-activated cell sorting of *Escherichia coli* expressing a functional antibody fragment on the external surface," Proc. Natl. Acad. Sci. USA, Nov. 15, 1993, vol. 90, No. 22, pp. 10444-10448.
Fried et al., "Equilibria and kinetics of lac repressor-operator interactions by polyacrylamide gel electrophoresis," Nucl. Acid Res., Dec. 11, 1981, vol. 9, No. 23, pp. 6505-6525.
Georgiou et al., "Display of heterologous proteins on the surface of microorganisms: From the screening of combinatorial libraries to live recombinant vaccines," Nat. Biotech., Jan. 1997, vol. 15, pp. 29-34.
Hanes et al., "In vitro selection and evolution of functional proteins by using ribosome display," PNAS, May 1997, vol. 34, pp. 4937-4942.
Heyduk et al., "Molecular Pincers: Antibody-Based Homogeneous Protein Sensors, " Anal. Chem., Jul. 1, 2008, vol. 80, No. 13, pp. 5152-5159.
Hosse et al., "A new generation of protein display scaffolds for molecular recognition," Protein Science, 2006, vol. 15 pp. 14-27.
Lass-Napiorkowska et al., "Detection Methodology Based on Target Molecule-Induced Sequence-Specific Binding to a Single-Stranded Oligonucleotide," Anal. Chem., 2012, vol. 84, pp. 3382-3389.
Notice of Allowance dated Aug. 5, 2014 from related U.S. Appl. No. 11/916,776, 7 pages.
Notice of Allowance dated Jun. 16, 2014 from related U.S. Appl. No. 13/728,226, 21 pages.
Notice of Allowance dated Aug. 19, 2014 from related Canadian Patent Application No. 2,661,198, 1 page.
Notice of Allowance and Interview Summary dated Dec. 20, 2012 for related U.S. Appl. No. 12/830,958, 16 pages.
Office Action dated May 8, 2012 for related U.S. Appl. No. 12/830,958; 21 pages.
Office Action dated Jun. 14, 2010 from related U.S. Appl. No. 11/916,776, 9 pages.
Office Action dated Jun. 17, 2011 from related U.S. Appl. No. 12/961,135, 17 pages.
Office Action dated Jun. 30, 2011 from related U.S. Appl. No. 11/916,776, 12 pages.
Office Action dated Mar. 12, 2009 from related U.S. Appl. No. 10/539,107, 23 pages.

(56) References Cited

OTHER PUBLICATIONS

Office Action dated Nov. 24, 2010 from related Japanese Patent Application No. 2006-543991, 2 pages (with 2 pages of English translation).
Office Action dated Oct. 10, 2011 from related Chinese Patent Application No. 200780037379.1, 7 pages ( with 7 page English translation).
Office Action dated Oct. 26, 2010 from related European Patent Application No. 078773908.3, 5 pages.
Office Action dated Sep. 14, 2009 from related U.S. Appl. No. 11/836,339, 16 pages.
Office Action dated Sep. 30, 2009 from related U.S. Appl. No. 11/836,333, 32 pages.
Office Action dated Sep. 8, 2011 from related Chinese Patent Application No. 200480036874.7, 4 pages (5 pages with English translation).
Office Action dated Mar. 8, 2010 from related U.S. Appl. No. 11/836,339, 14 pages.
Oligonucleotide Modifications (TriLink Products) screen from http://www.trilinkbiotech.com/products/oligo/details_modifications_asp?ProducUD=133, printed Sep. 8, 2009; 1 page.
Office Action dated Apr. 4, 2011 from related European Patent Application No. 06770407.2, 3 pages.
Office Action dated Aug. 9, 2010 from related Chinese Patent Application No. 200480036874.7, 9 pages (14 pages of English translation).
Office Action dated Dec. 1, 2011 from related U.S. Appl. No. 12/961,135, 23 pages.
Office Action dated Dec. 18, 2008 from related European Patent Application No. 04813618.8, 3 pages.
Office Action dated Dec. 18, 2009 from related U.S. Appl. No. 10/539,107, 22 pages.
Office Action dated Feb. 3, 2011 from related Canadian Patent Application No. 2,575,006, 5 pages.
Office Action dated Jan. 4, 2012 from related European Patent Application No. 07873908.3, 3 pages.
Office Action dated Jan. 19, 2011 from related Chinese Patent Application No. 200480036874.7, 5 pages (with 7 pages English translation).
Office Action dated Jul. 1, 2008 from related European Patent Application No. 04813618.8, 3 pages.
Office Action dated Jul. 2, 2008 from related U.S. Appl. No. 10/539,107, 21 pages.
Office Action dated Feb. 23, 2010 from related Japanese Patent Application No. 2006-543991, 3 pages (with 3 pages of English translation).
Office Action dated May 27, 2013 from related Chinese Patent Application No. 200980146720.6 (with 18 pages of English translation).
Office Action dated Dec. 10, 2013 from related Chinese Patent Application No. 200980146720.6; 34 pages including English translation.
Office Action dated May 20, 2014 from related Chinese Patent Application No. 200980146720.6, 25 pages, including English translation.
Office Action dated Jul. 29, 2014 from related Japanese Patent Application No. 2011-284014; 1 page (English translation only).
Office Action dated Oct. 8, 2013 from related Japanese Patent Application No. 2011-284014; 2 pages (English translation only).
Office Action dated Aug. 21, 2013 from related Canadian Patent Application No. 2,660,129, 3 pages.
Office Action dated Feb. 19, 2014 from related Canadian Patent Application No. 2,787,483, 3 pages.
Office Action dated Aug. 30, 2013 from related Canadian Patent Application No. 2,611,198, 2 pages.
Office Action dated Dec. 27, 2013 from related Canadian Patent Application No. 2,744,003, 2 pages.
Office Action dated Mar. 26, 2013 from related Canadian Patent Application No. 2,744,003, 3 pages.
Office Action dated Nov. 27, 2013 from related Indian Patent Application No. 1337/CHENP/2009; 4 pages.
Office Action dated Sep. 13, 2013 from related U.S. Appl. No. 13/578,718, 24 pages.
Office Action with Interview Summary dated Feb. 21, 2014 from related U.S. Appl. No. 13/578,718, 32 pages.
Office Action dated Jan. 10, 2014 from related U.S. Appl. No. 13/728,226, 30 pages.
Order Rescheduling Oral Proceedings dated Jan. 28, 2014 from related European Patent Application No. 348136918.8, 1 page.

BIOSENSOR FOR DETECTING MULTIPLE EPITOPES ON A TARGET

CROSS REFERENCE TO RELATED APPLICATIONS

This application in a continuation of U.S. application Ser. No. 13/133,198, filed Oct. 18, 2011, now U.S. Pat. No. 8,993,245, issued Mar. 31, 2015, which is a U.S. National Application of PCT Application number PCT/US2009/065142, filed Nov. 19, 2009, which claims the priority of U.S. Provisional Application No. 61/116,875, filed Nov. 21, 2008, each of which is hereby incorporated by reference in its entirety.

GOVERNMENTAL RIGHTS

This invention was made with government support under R41 GM079891 awarded by the National Institutes of Health. The government has certain rights in the invention.

BACKGROUND OF THE INVENTION

Pathogenic bacteria are responsible for over fifty infectious diseases. Methodologies allowing detection of the pathogens in clinical, food, water and environmental samples are an important component of infectious disease diagnosis, treatment and prevention. Currently, pathogen detection involves traditional methods based on cell culture and colony counting, antigen detection methods, PCR-based methods, and various biosensors. Each of these methods has its own strengths and weaknesses. Traditional methods are robust and sensitive, but very slow. Antigen and PCR-based methods are much faster but are technically demanding and in the case of PCR-based methods, prone to false-positives. Biosensors offer the promise of much shorter detection times but require more development before they become a real alternative. There is clearly a need for new detection methodologies that would overcome the limitations of currently existing technologies.

SUMMARY OF THE INVENTION

One aspect of the present invention encompasses a method for detecting a target comprising at least one repeating epitope. The method comprises contacting a sample comprising the target with a molecular biosensor. The biosensor comprises:

$R^{24}$—$R^{25}$—$R^{26}$—$R^{27}$, $R^{28}$—$R^{29}$—$R^{30}$—$R^{31}$, and

O wherein:

- $R^{24}$ is a peptide epitope binding agent that binds to a repeating epitope on a target antibody;
- $R^{25}$ is a flexible linker attaching $R^{24}$ to $R^{26}$;
- $R^{26}$ and $R^{30}$ are a pair of nucleotide sequences that are not complementary to each other, but are complementary to two distinct regions on O;
- $R^{27}$ and $R^{31}$ together comprise a detection means such that when $R^{26}$ and $R^{30}$ associate with O a detectable signal is produced;
- $R^{28}$ is a peptide epitope binding agent that binds to the same repeating epitope on the target antibody as $R^{24}$;
- $R^{29}$ is a flexible linker attaching $R^{28}$ to $R^{30}$; and

- O is a nucleotide sequence comprising a first region that is complementary to $R^{26}$, and a second region that is complementary to $R^{30}$, and detecting the signal produced by the association of $R^{26}$ with O and $R^{30}$ with O, wherein the signal indicates the presence of the target antibody.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION OF THE INVENTION

Figure 1A:
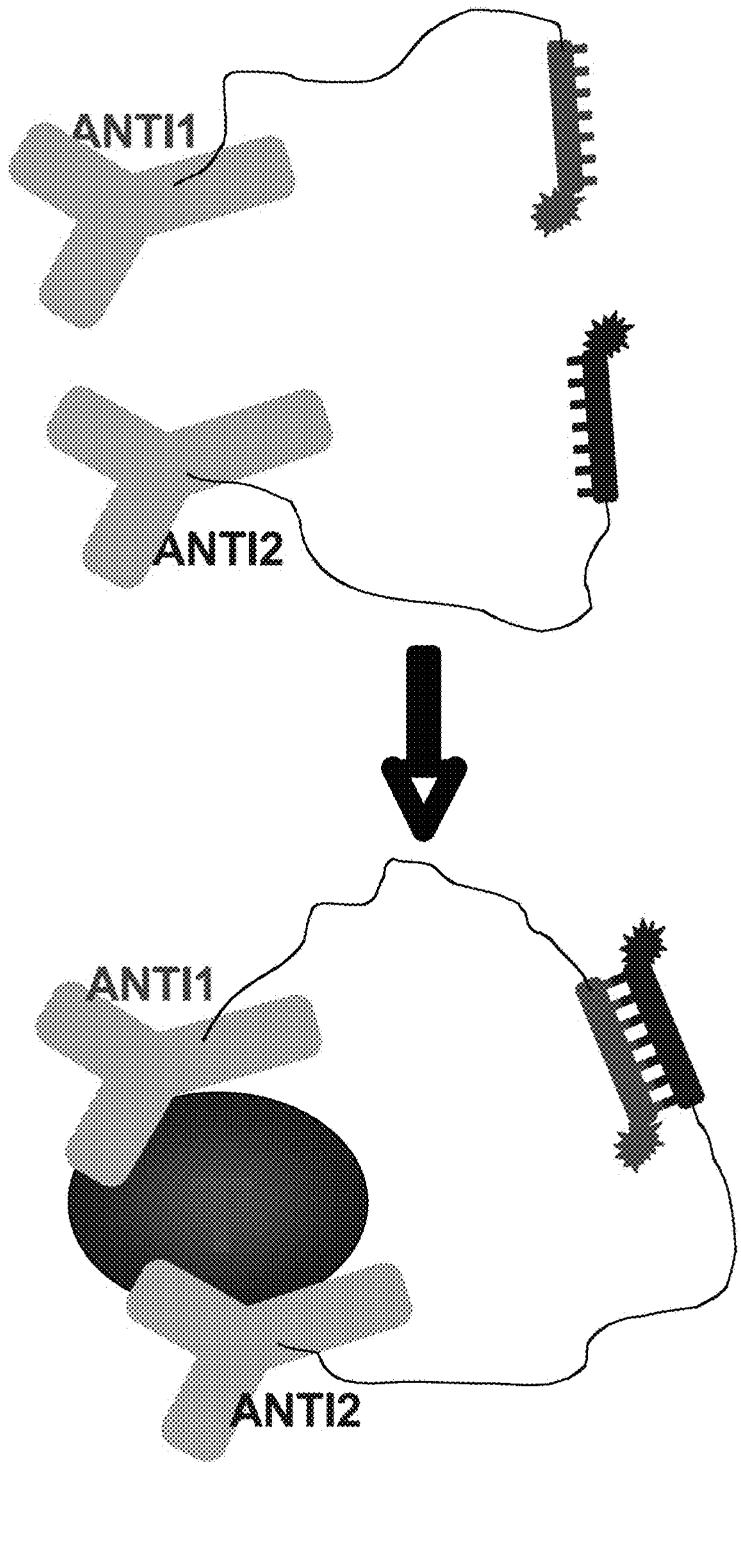
FIG. 1A depicts the design of a molecular biosensor. ANTI1 and ANTI2 depict antibodies labeled with signaling oligonucleotides. T corresponds to the target protein.

The present invention is directed to a method of using a molecular biosensor. In particular, the method comprises detecting targets comprising repeating epitopes. The method typically involves target-molecule induced co-association of two epitope-binding agents that each recognize the same repeating epitope on the target. The epitope-binding agents each comprise complementary signaling oligonucleotides that are labeled with detection means and are attached to the epitope binding agents through a flexible linker. Co-association of the two epitope-binding agents with the target results in bringing the two signaling oligonucleotides into proximity such that a detectable signal is produced. Advantageously, the molecular biosensors provide a rapid homogeneous means to detect a variety of targets comprising repeating epitopes, including but not limited to proteins, carbohydrates, lipids, and microbial organisms.

I. Molecular Biosensors

One aspect of the invention, accordingly, encompasses a molecular biosensor. In one embodiment, the molecular biosensor may be monovalent comprising a single epitope binding agent that binds to an epitope on a target. A molecular biosensor of the invention, however, is typically multivalent. It will be appreciated by a skilled artisan, depending upon the target, that the molecular biosensor may comprise from about 2 to about 5 epitope binding agents. Typically, the molecular biosensor may comprise 2 or 3 epitope binding agents and more typically, may comprise 2 epitope binding agents. In one alternative of this embodiment, therefore, the molecular biosensor may be bivalent comprising a first epitope binding agent that binds to a repeating epitope on a target and a second epitope binding agent that binds to the same repeating epitope on the target. In another alternative of this embodiment, the molecular biosensor may be trivalent comprising a first epitope binding agent that binds to a repeating epitope on a target, a second epitope binding agent that binds to the same repeating epitope on a target and a third epitope binding agent that binds to the same repeating epitope on a target.

(a) Bivalent Molecular Sensors

In one embodiment of the invention, the molecular biosensor may be bivalent. In a typical embodiment, the bivalent construct will comprise a first epitope binding agent that binds to a repeating epitope on a target, a first linker, a first signaling oligo, a first detection means, a second epitope binding agent that binds to the same repeating epitope on the target, a second linker, a second signaling oligo, and a second detection means.

In one preferred embodiment, the molecular biosensor comprises two nucleic acid constructs, which together have formula (I):

$$R^1—R^2—R^3—R^4; \text{ and}$$

$$R^5—R^6—R^7—R^8; \qquad (I)$$

wherein:

- $R^1$ is an epitope binding agent that binds to a repeating epitope on a target;
- $R^2$ is a flexible linker attaching $R^1$ to $R^3$;
- $R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
- $R^4$ and $R^8$ together comprise a detection means such that when $R^3$ and $R^7$ associate a detectable signal is produced;
- $R^5$ is an epitope binding agent that binds to the same repeating epitope on the target as $R^1$; and
- $R^6$ is a flexible linker attaching $R^5$ to $R^7$.

As will be appreciated by those of skill in the art, the choice of epitope binding agents, $R^1$ and $R^5$, in molecular biosensors having formula (I) can and will vary depending upon the particular target. By way of example, when the target is a protein, $R^1$ and $R^5$ may be an aptamer, or antibody. By way of further example, when $R^1$ and $R^5$ are double stranded nucleic acid the target is typically a macromolecule that binds to DNA or a DNA binding protein. In general, suitable choices for $R^1$ and $R^5$ will include two agents that each recognize a repeating epitope on the same target. In certain embodiments, however, it is also envisioned that $R^1$ and $R^5$ may recognize repeating epitopes on different targets. Non-limiting examples of suitable epitope binding agents, depending upon the target, include agents selected from the group consisting of an aptamer, an antibody, an antibody fragment, a double-stranded DNA sequence, a ligand, a ligand fragment, a receptor, a receptor fragment, a polypeptide, a peptide, a coenzyme, a coregulator, an allosteric molecule, and an ion. In an exemplary embodiment, $R^1$ and $R^5$ are each antibodies selected from the group consisting of polyclonal antibodies, ascites, Fab fragments, Fab' fragments, monoclonal antibodies, chimeric antibodies, and humanized antibodies. In a preferred embodiment, $R^1$ and $R^5$ are each monoclonal antibodies. In another embodiment, $R^1$ and $R^5$ are each aptamers. In an additional embodiment, $R^1$ and $R^5$ are each double stranded DNA. In a further embodiment, $R^1$ is a double stranded nucleic acid and $R^5$ is an aptamer. In an additional embodiment, $R^1$ is an antibody and $R^5$ is an aptamer. In an additional embodiment, $R^1$ is an antibody and $R^5$ is a double stranded DNA. In embodiments where $R^1$ and $R^5$ comprise the same epitope binding agent, the bivalent biosensor may be considered a monovalent biosensor.

In an additional embodiment for molecular biosensors having formula (I), exemplary linkers, $R^2$ and $R^6$, will functionally keep $R^3$ and $R^7$ in close proximity such that when $R^1$ and $R^5$ each bind to the target, $R^3$ and $R^7$ associate in a manner such that a detectable signal is produced by the detection means, $R^4$ and $R^8$. $R^2$ and $R^6$ may each be a nucleotide sequence from about 10 to about 100 nucleotides in length. In one embodiment, $R^2$ and $R^6$ are from 10 to about 25 nucleotides in length. In another embodiment, $R^2$ and $R^6$ are from about 25 to about 50 nucleotides in length. In a further embodiment, $R^2$ and $R^6$ are from about 50 to about 75 nucleotides in length. In yet another embodiment, $R^2$ and $R^6$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^2$ and $R^6$ are comprised of DNA bases. In another embodiment, $R^2$ and $R^6$ are comprised of RNA bases. In yet another embodiment, $R^2$ and $R^6$ are comprised of modified nucleic acid bases, such as modified DNA bases or modified RNA bases. Examples of suitable modified DNA or RNA bases include 2'-fluoro nucleotides, 2'-amino nucleotides, 5'-aminoallyl-2'-fluoro nucleotides and phosphorothioate nucleotides. Alternatively, $R^2$ and $R^6$ may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, $R^2$ and $R^6$ are from 0 to about 500 angstroms in length. In another embodiment, $R^2$ and $R^6$ are from about 20 to about 400 angstroms in length. In yet another embodiment, $R^2$ and $R^6$ are from about 50 to about 250 angstroms in length.

In a further embodiment for molecular biosensors having formula (I), $R^3$ and $R^7$ are complementary nucleotide sequences having a length such that they preferably do not associate unless $R^1$ and $R^5$ bind to separate repeating epitopes on the target. When $R^1$ and $R^5$ bind to separate epitopes of the target, $R^3$ and $R^7$ are brought to relative proximity resulting in an increase in their local concentration, which drives the association of $R^3$ and $R^7$. $R^3$ and $R^7$ may be from about 2 to about 20 nucleotides in length. In another embodiment, $R^3$ and $R^7$ are from about 4 to about 15 nucleotides in length. In an exemplary embodiment, $R^3$ and $R^7$ are from about 5 to about 7 nucleotides in length. In one embodiment, $R^3$ and $R^7$ have a free energy for association from about 5.5 kcal/mole to about 8.0 kcal/mole as measured in the selection buffer conditions, defined below. In another embodiment, $R^3$ and $R^7$ have a free energy for association from about 6.0 kcal/mole to about 8.0 kcal/mole as measured in the selection buffer conditions defined below. In yet another embodiment, $R^3$ and $R^7$ have a free energy for association from about 7.0 kcal/mole to 8.0 kcal/mole in the selection buffer conditions. In a preferred embodiment, $R^3$ and $R^7$ have a free energy for association of 7.5 kcal/mole in the selection buffer conditions described below. Preferably, in each embodiment $R^3$ and $R^7$ are not complementary to $R^1$ and $R^5$.

In a typical embodiment for molecular biosensors having formula (I), $R^4$ and $R^5$ may together comprise several suitable detection means such that when $R^3$ and $R^7$ associate, a detectable signal is produced. Exemplary detections means suitable for use in the molecular biosensors may include FRET, fluorescence cross-correlation spectroscopy, flourescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

In a further embodiment, the molecular biosensor will have formula (I) wherein:

$R^1$ is an epitope binding agent that binds to a repeating epitope on a target and is selected from the group consisting of an aptamer, an antibody, and double stranded nucleic acid;

$R^2$ is a flexible linker attaching $R^1$ to $R^3$ by formation of a covalent bond with each of $R^1$ and $R^3$, wherein $R^2$ comprises a bifunctional chemical cross linker and is from 0 to 500 angstroms in length;

$R^3$ and $R^7$ are a pair of complementary nucleotide sequences from about 4 to about 15 nucleotides in length and having a free energy for association from about 5.5 kcal/mole to about 8.0 kcal/mole at a temperature from about 21° C. to about 40° C. and at a salt concentration from about 1 mM to about 100 mM;

$R^4$ and $R^5$ together comprise a detection means selected from the group consisting of FRET, fluorescence cross-correlation spectroscopy, flourescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes;

$R^5$ is an epitope binding agent that binds to the same repeating epitope on the target as $R^1$, and is selected from the group consisting of an aptamer, an antibody, and double stranded nucleic acid; and $R^6$ is a flexible linker attaching $R^5$ to $R^7$ by formation of a covalent bond with each of $R^5$ and $R^7$, wherein $R^6$ comprises a bifunctional chemical cross linker and is from 0 to 500 angstroms in length.

Yet another embodiment of the invention encompasses a molecular biosensor having formula (I) wherein:

$R^1$ is an antibody that binds to a repeating epitope on a target;

$R^2$ is a flexible linker attaching $R^1$ to $R^3$;

$R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means such that when $R^3$ and $R^7$ associate a detectable signal is produced;

$R^5$ is an antibody that binds to the same repeating epitope on the target as $R^1$; and $R^6$ is a flexible linker attaching $R^5$ to $R^7$.

A further embodiment of the invention encompasses a molecular biosensor having formula (I) wherein:

$R^1$ is an antibody that binds to a repeating epitope on a target;

$R^2$ is a flexible linker attaching $R^1$ to $R^3$ by formation of a covalent bond with each of $R^1$ and $R^3$, wherein $R^2$ comprises a bifunctional chemical cross linker and is from 0 to 500 angstroms in length;

$R^3$ and $R^7$ are a pair of complementary nucleotide sequence from about 4 to about 15 nucleotides in length and having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means selected from the group consisting of FRET, fluorescence cross-correlation spectroscopy, flourescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes;

$R^5$ is an antibody that binds to the same repeating epitope on the target; and $R^6$ is a flexible linker attaching $R^5$ to $R^7$ by formation of a covalent bond with each of $R^5$ and $R^7$, wherein $R^6$ comprises a bifunctional chemical cross linker and is from 0 to 500 angstroms in length.

(b) Trivalent Molecular Sensors

In an additional alternative embodiment, the molecular biosensor may be trivalent. In a typical embodiment, the trivalent construct may comprise a first epitope binding agent that binds to a repeating epitope on a target, a first linker, a first signaling oligo, a first detection means, a second epitope binding agent that binds to the same repeating epitope on the target, a second linker, a second signaling oligo, a second detection means, a third epitope binding agent that binds to the same repeating epitope on a target, a third linker, a third signaling oligo, and a third detection means.

In one preferred embodiment, the molecular biosensor comprises three nucleic acid constructs, which together have formula (II):

$$R^{15}—R^{14}—R^{13}—R^{9}—R^{10}—R^{11}—R^{12};$$

$$R^{16}—R^{17}—R^{18}—R^{19};\text{ and}$$

$$R^{20}—R^{21}—R^{22}—R^{23} \qquad \text{(II)}$$

wherein:

$R^9$ is an epitope binding agent that binds to a repeating epitope on a target;

$R^{10}$ is a flexible linker attaching $R^9$ to $R^{11}$;

$R^{11}$ and $R^{22}$ are a first pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^{12}$ and $R^{23}$ together comprise a detection means such that when $R^{11}$ and $R^{22}$ associate a detectable signal is produced;

$R^{13}$ is a flexible linker attaching $R^9$ to $R^{14}$;

$R^{14}$ and $R^{18}$ are a second pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^{15}$ and $R^{19}$ together comprise a detection means such that when $R^{14}$ and $R^{18}$ associate a detectable signal is produced;

$R^{16}$ is an epitope binding agent that binds to the same repeating epitope on a target as $R^9$;

$R^{17}$ is a flexible linker attaching $R^{16}$ to $R^{18}$;

$R^{20}$ is an epitope binding agent that binds to the same repeating epitope on a target as $R^9$ and $R^{16}$; and $R^{21}$ is a flexible linker attaching $R^{20}$ to $R^{22}$.

The choice of epitope binding agents, $R^9$, $R^{16}$ and $R^{20}$, in molecular biosensors having formula (II) can and will vary depending upon the particular target. Generally speaking, suitable choices for $R^9$, $R^{16}$ and $R^{20}$ will include three agents that each recognize the same repeating epitope on the same target or on different targets. Non-limiting examples of suitable epitope binding agents, depending upon the target(s), include agents selected from the group consisting of an aptamer, an antibody, an antibody fragment, a double-stranded DNA sequence, a ligand, a ligand fragment, a receptor, a receptor fragment, a polypeptide, a peptide, a coenzyme, a coregulator, an allosteric molecule, and an ion. In an exemplary embodiment, $R^9$, $R^{16}$ and $R^{20}$ are each antibodies.

In an additional embodiment for molecular biosensors having formula (II), exemplary linkers, $R^{10}$ and $R^{21}$, will functionally keep $R^{11}$ and $R^{22}$ in close proximity such that when $R^9$ and $R^{20}$ each bind to the repeating epitopes on the target(s), $R^{11}$ and $R^{22}$ associate in a manner such that a detectable signal is produced by the detection means, $R^{12}$ and $R^{23}$. In addition, exemplary linkers, $R^{13}$ and $R^{17}$, will functionally keep $R^{14}$ and $R^{18}$ in close proximity such that when $R^9$ and $R^{16}$ each bind to the repeating epitopes on the target(s), $R^{14}$ and $R^{18}$ associate in a manner such that a detectable signal is produced by the detection means, $R^{15}$ and $R^{19}$. In one embodiment, the linkers utilized in molecular biosensors having formula (II) may each be a nucleotide sequence from about 10 to about 100 nucleotides in length. In one embodiment, the linkers are from 10 to about 25 nucleotides in length. In another embodiment, the linkers are from about 25 to about 50 nucleotides in length. In a further embodiment, the linkers are from about 50 to about 75 nucleotides in length. In yet another embodiment, the linkers are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment, the linkers are comprised of DNA bases. In another embodiment, the linkers are comprised of RNA bases. In yet another embodiment, the linkers are comprised of modified nucleic acid bases, such as modified DNA bases or modified RNA bases. Examples of suitable modified DNA or RNA bases include 2'-fluoro nucleotides, 2'-amino nucleotides, 5'-aminoallyl-2'-fluoro nucleotides and phosphorothioate nucleotides. Alternatively, the linkers may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, the linkers are from 0 to about 500 angstroms in length. In another embodiment, the linkers are from about 20 to about 400 angstroms in length. In yet another embodiment, the linkers are from about 50 to about 250 angstroms in length.

In a further embodiment for molecular biosensors having formula (II), $R^{11}$ and $R^{22}$ are complementary nucleotide sequences having a length such that they preferably do not associate unless $R^9$ and $R^{20}$ bind to separate repeating epitopes on the target(s). In addition, $R^{14}$ and $R^{18}$ are complementary nucleotide sequences having a length such that they preferably do not associate unless $R^9$ and $R^{16}$ bind to separate repeating epitopes on the target(s). $R^{11}$ and $R^{22}$ and $R^{14}$ and $R^{18}$ may be from about 2 to about 20 nucleotides in length. In another embodiment, $R^{11}$ and $R^{22}$ and $R^{14}$ and $R^{18}$ are from about 4 to about 15 nucleotides in length. In an exemplary embodiment, $R^{11}$ and $R^{22}$ and $R^{14}$ and $R^{18}$ are from about 5 to about 7 nucleotides in length. In one embodiment, $R^{11}$ and $R^{22}$ and $R^{14}$ and $R^{18}$ have a free energy for association from about 5.5 kcal/mole to about 8.0 kcal/mole as measured in the selection buffer conditions, defined below. In another embodiment, $R^{11}$ and $R^{22}$ and $R^{14}$ and $R^{18}$ have a free energy for association from about 6.0 kcal/mole to about 8.0 kcal/mole as measured in the selection buffer conditions defined below. In yet another embodiment, $R^{11}$ and $R^{22}$ and $R^{14}$ and $R^{18}$ have a free energy for association from about 7.0 kcal/mole to 8.0 kcal/mole in the selection buffer conditions. In a preferred embodiment, $R^{11}$ and $R^{22}$ and $R^{14}$ and $R^{18}$ have a free energy for association of 7.5 kcal/mole in the selection buffer conditions described below. Preferably, in each embodiment $R^{11}$ and $R^{22}$ and $R^{14}$ and $R^{18}$ are not complementary to any of $R^9$, $R^{16}$ or $R^{20}$.

In a typical embodiment for molecular biosensors having formula (II), $R^{12}$ and $R^{23}$ may together comprise several suitable detection means such that when $R^{11}$ and $R^{22}$ associate, a detectable signal is produced. In addition, $R^{15}$ and $R^{19}$ may together comprise several suitable detection means such that when $R^{14}$ and $R^{18}$ associate, a detectable signal is produced. Exemplary detections means suitable for use in the molecular biosensors include FRET, fluorescence cross-correlation spectroscopy, flourescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

(c) Three-Component Molecular Biosensors

Another embodiment of the invention comprises three-component molecular biosensors. These biosensors, in addition to having at least two epitope binding agent constructs, further comprise an oligonucleotide construct, referred to below as "O." In certain embodiments, the three-component molecular biosensor will comprise an endonuclease restriction site. In alternative embodiments, the three-component molecular biosensor will not have an endonuclease restriction site.

i. Biosensors with No Endonuclease Restriction Site

In one embodiment, the three-component biosensor will comprise: (1) a first epitope binding agent construct that binds to a repeating epitope on a target, a first linker, a first signaling oligo, and a first detection means; (2) a second epitope binding agent construct that binds to the same repeating epitope on the target, a second linker, a second signaling oligo, and a second detection means; and (3) an oligonucleotide construct that comprises a first region that is complementary to the first oligo and a second region that is complementary to the second oligo. The first signaling oligo and second signaling oligo, as such, are not complementary to each other, but are complementary to two distinct regions on the oligonucleotide construct. Co-association of the two epitope-binding agent constructs with the target results in hybridization of each signaling oligos to the oligonucleotide construct. Binding of the two signaling oligo to the oligonucleotide construct brings them into proximity such that a detectable signal is produced.

In an exemplary embodiment, the three-component molecular biosensor comprises three nucleic acid constructs, which together have formula (III):

$$R^{24}—R^{25}—R^{26}—R^{27};$$

$$R^{28}—R^{29}—R^{30}—R^{31};$$

$$O \quad \text{(III)}$$

wherein:

- $R^{24}$ is an epitope-binding agent that binds to repeating epitope on a target;
- $R^{25}$ is a flexible linker attaching $R^{24}$ to $R^{26}$;
- $R^{26}$ and $R^{30}$ are a pair of nucleotide sequences that are not complementary to each other, but are complementary to two distinct regions on O;
- $R^{27}$ and $R^{31}$ together comprise a detection means such that when $R^{26}$ and $R^{30}$ associate a detectable signal is produced;
- $R^{28}$ is an epitope-binding agent that binds to the same epitope on the target as $R^{24}$;
- $R^{29}$ is a flexible linker attaching $R^{28}$ to $R^{30}$; and
- O is a nucleotide sequence comprising a first region that is complementary to $R^{26}$, and a second region that is complementary to $R^{30}$.

The choice of epitope binding agents, $R^{24}$ and $R^{28}$, in molecular biosensors having formula (III) can and will vary depending upon the particular target. By way of example, when the target is a protein, $R^{24}$ and $R^{28}$ may be an aptamer, or antibody. By way of further example, when $R^{24}$ and $R^{28}$ are double stranded nucleic acid the target is typically a macromolecule that binds to DNA or a DNA binding protein. In general, suitable choices for $R^{24}$ and $R^{28}$ will include two agents that each recognize the same repeating epitope on the same target. In certain embodiments, however, it is also envisioned that $R^{24}$ and $R^{28}$ may recognize distinct epitopes on different targets. Non-limiting examples of suitable epitope binding agents, depending upon the target, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In an exemplary embodiment, $R^{24}$ and $R^{28}$ are each antibodies selected from the group consisting of polyclonal antibodies, ascites, Fab fragments, Fab' fragments, monoclonal antibodies, chimeric antibodies, and humanized antibodies. In another embodiment, $R^{24}$ and $R^{28}$ are each aptamers. In an alternative embodiment, $R^{24}$ and $R^{28}$ are peptides. In a preferred alternative of this embodiment, $R^{24}$ and $R^{28}$ are each monoclonal antibodies. In an additional embodiment, $R^{24}$ and $R^{28}$ are each double stranded DNA. In a further embodiment, $R^{24}$ is a double stranded nucleic acid and $R^{28}$ is an aptamer. In an additional embodiment, $R^{24}$ is an antibody and $R^{28}$ is an aptamer. In another additional embodiment, $R^{24}$ is an antibody and $R^{28}$ is a double stranded DNA.

In an additional embodiment for molecular biosensors having formula (III), exemplary linkers, $R^{25}$ and $R^{29}$ may each be a nucleotide sequence from about 10 to about 100 nucleotides in length. In one embodiment, $R^{25}$ and $R^{29}$ are from 10 to about 25 nucleotides in length. In another embodiment, $R^{2}$ and $R^{6}$ are from about 25 to about 50 nucleotides in length. In a further embodiment, $R^{25}$ and $R^{29}$ are from about 50 to about 75 nucleotides in length. In yet another embodiment, $R^{25}$ and $R^{29}$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^{25}$ and $R^{29}$ are comprised of DNA bases. In another embodiment, $R^{25}$ and $R^{29}$ are comprised of RNA bases. In yet another embodiment, $R^{25}$ and $R^{29}$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^{25}$ and $R^{29}$ may be nucleotide mimics. Examples of nucleotide mimics include locked nucleic acids (LNA), peptide nucleic acids (PNA), and phosphorodiamidate morpholino oligomers (PMO).

Alternatively, $R^{25}$ and $R^{29}$ may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP(N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, $R^{25}$ and $R^{29}$ are from 0 to about 500 angstroms in length. In another embodiment, $R^{25}$ and $R^{29}$ are from about 20 to about 400 angstroms in length. In yet another embodiment, $R^{25}$ and $R^{29}$ are from about 50 to about 250 angstroms in length.

In a further embodiment for molecular biosensors having formula (III), $R^{26}$ and $R^{30}$ are nucleotide sequences that are not complementary to each other, but that are complementary to two distinct regions of 0. $R^{26}$ and $R^{30}$ may be from about 2 to about 20 nucleotides in length. In another embodiment, $R^{26}$ and $R^{30}$ are from about 4 to about 15 nucleotides in length. In an exemplary embodiment, $R^{26}$ and $R^{30}$ are from about 5 to about 7 nucleotides in length. Preferably, in each embodiment $R^{26}$ and $R^{30}$ are not complementary to $R^{24}$ and $R^{28}$.

In a typical embodiment for molecular biosensors having formula (III), $R^{27}$ and $R^{31}$ may together comprise several suitable detection means such that when $R^{26}$ and $R^{30}$ each bind to complementary, distinct regions on O, a detectable signal is produced. Exemplary detections means suitable for use in the molecular biosensors include fluorescent resonance energy transfer (FRET), lanthamide resonance energy transfer (LRET), fluorescence cross-correlation spectroscopy, flourescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes.

For molecular biosensors having formula (III), O comprises a first region that is complementary to $R^{26}$, and a second region that is complementary to $R^{30}$. O may be from about 8 to about 100 nucleotides in length. In other embodiments, 0 is from about 10 to about 15 nucleotides in length, or from about 15 to about 20 nucleotides in length, or from about 20 to about 25 nucleotides in length, or from about 25 to about 30 nucleotides in length, or from about 30 to about 35 nucleotides in length, or from about 35 to about 40 nucleotides in length, or from about 40 to about 45 nucleotides in length, or from about 45 to about 50 nucleotides in length, or from about 50 to about 55 nucleotides in length, or from about 55 to about 60 nucleotides in length, or from about 60 to about 65 nucleotides in length, or from about 65 to about 70 nucleotides in length, or from about 70 to about 75 nucleotides in length, or from about 75 to about 80 nucleotides in length, or from about 80 to about 85 nucleotides in length, or from about 85 to about 90 nucleotides in length, or from about 90 to about 95 nucleotides in length, or greater than about 95 nucleotides in length.

In an exemplary embodiment, 0 will comprise formula (IV):

$$R^{32}—R^{33}—R^{34}—R^{35}—R^{36} \quad \text{(IV)}$$

wherein:

$R^{32}$, $R^{34}$, and $R^{36}$ are nucleotide sequences not complementary to any of $R^{26}$, $R^{30}$, $R^{33}$, or $R^{35}$. $R^{32}$, $R^{34}$, and $R^{36}$ may independently be from about 2 to about 20 nucleotides in length. In other embodiments, $R^{32}$, $R^{34}$, and $R^{36}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;

$R^{33}$ is a nucleotide sequence complementary to $R^{26}$, and $R^{35}$ is a nucleotide sequence that is complementary to $R^{30}$.

$R^{33}$ and $R^{35}$ generally have a length such that the free energy of association between $R^{33}$ and $R^{26}$ and $R^{35}$ and $R^{30}$ is from about −5 to about −12 kcal/mole at a temperature from about 21° C. to about 40° C. and at a salt concentration from about 1 mM to about 100 mM. In other embodiments, the free energy of association between $R^{33}$ and $R^{26}$ and $R^{35}$ and $R^{30}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{33}$ and $R^{35}$ may range from about 4 to about 20 nucleotides in length. In other embodiments, $R^{33}$ and $R^{35}$ may about 4, about 5, about 6, about 7, about 8, about 9, about 10, about 11, about 12, about 13, about 14, about 15, about 16, about 17, about 18, about 19, or greater than about 10 nucleotides in length.

ii. Biosensors with an Endonuclease Restriction Site

In an alternative embodiment, the three-component biosensor will comprise: (1) a first epitope binding agent construct that binds to a repeating epitope on a target, a first linker, and a first signaling oligo; (2) a second epitope binding agent construct that binds to the same repeating epitope on the target, a second linker, a second signaling oligo and (3) an oligonucleotide construct that comprises a first region that is complementary to the first oligo, a second region that is complementary to the second oligo, two flexible linkers, an endonuclease restriction site overlapping the first and the second regions complementary to the first and the second oligos, and a pair of complementary nucleotides with detection means. The first signaling oligo and second signaling oligo are not complementary to each other, but are complementary to two distinct regions on the oligonucleotide construct. When the oligonucleotide construct is intact, the complementary nucleotides are annealed and produce a detectable signal. Co-association of the two epitope-binding agent constructs with the target results in hybridization of each signaling oligo to the oligonucleotide construct. The signaling oligos hybridize to two distinct locations on the oligonucleotide construct such that a double-stranded DNA molecule containing the restriction site is produced, with a gap between the signaling oligos located exactly at the site of endonuclease cleavage in one strand of the double-stranded DNA substrate. When a restriction endonuclease is present, accordingly, it will cleave the oligonucleotide construct only when the target is present (i.e., when the signaling oligos are bound to the oligonucleotide construct). Upon this cleavage, the detection means present on the oligonucleotide are separated-resulting in no detectable signal. Upon dissociation of the cleaved oligonucleotide construct, another oligonucleotide construct may hybridize with the signaling oligos of the two epitope-binding agents co-associated with the target and the cleavage reaction may be repeated. This cycle of hybridization and cleavage may be repeated many times resulting in cleavage of multiple oligonucleotide constructs per one complex of the two epitope-binding agents with the target.

In an exemplary alternative of this embodiment, the three-component molecular biosensor comprises three nucleic acid constructs, which together have formula (V):

$R^{36}—R^{37}R^{38}$;

$R^{39}—R^{40}—R^{41}$;

O (V)

wherein:

$R^{36}$ is an epitope-binding agent that binds to a repeating epitope on a target;

$R^{37}$ is a flexible linker attaching $R^{36}$ to $R^{38}$;

$R^{38}$ and $R^{41}$ are a pair of nucleotide sequences that are not complementary to each other, but are complementary to two distinct regions on O;

$R^{39}$ is an epitope-binding agent that binds to the same repeating epitope on the target;

$R^{40}$ is a flexible linker attaching $R^{39}$ to $R^{41}$; and O comprises:

$R^{42}—R^{43}—R^{44}—R^{45}—R^{46}$ $R^{42}$ is a nucleotide construct comprising an endonuclease restriction site, a first region that is complementary to $R^{38}$, and a second region that is complementary to $R^{41}$.

$R^{43}$ is a first flexible linker;

$R^{44}$ is a first nucleotide sequence that is complementary to $R^{46}$ attached to a detection means;

$R^{45}$ is a second flexible linker;

$R^{46}$ is a second nucleotide sequence that is complementary to $R^{44}$ attached to a second detection means; and $R^{43}$ attaches $R^{42}$ to $R^{44}$ and $R^{45}$ attaches $R^{42}$ to $R^{46}$.

Suitable linkers, epitope binding agents, and detection means for three-component molecular biosensors having formula (V) are the same as three component molecular biosensors having formula (III). Suitable, endonuclease restriction sites comprising $R^{42}$ include sites that are recognized by restriction enzymes that cleave double stranded nucleic acid, but not single stranded nucleic acid. By way of non-limiting example, these sites may include AccI, AgeI, BamHI, BgI, BgII, BsiWI, BstBI, ClaI, CviQI, DdeI, DpnI, DraI, EagI, EcoRI, EcoRV, FseI, FspI, HaeII, HaeIII, HhaI, Hinc II, HinDIII, HpaI, HpaII, KpnI, KspI, MboI, MfeI, NaeI, NarI, NcoI, NdeI, NheI, NotI, PhoI, PstI, PvuI, PvuII, SacI, SacII, SalI, SbfI, SmaI, SpeI, SphI, StuI, TaqI, TfiI, TlII, XbaI, XhoI, XmaI, XmnI, and ZraI. Optionally, $R^{42}$ may comprise nucleotide spacers that precede or follow one or more of the endonuclease restriction site, the first region that is complementary to $R^{38}$, and/or the second region that is complementary to $R^{41}$. Suitable nucleotide spacers, for example, are detailed in formula (IV).

II. Methods of Using the Molecular Biosensors

A further aspect of the invention encompasses the use of the molecular biosensors of the invention in several applications. In certain embodiments, the molecular biosensors are utilized in methods for detecting one or more targets. In other embodiments, the molecular biosensors may be utilized in kits and for therapeutic applications.

Typically, a signal produced by a biosensor of the invention may be detectable in about 1, 2, 3, 4, 5, 6, 7, 8, 9, or 10 minutes. In certain embodiments, 80% of the maximum signal may be produced in about 3, 4, 5, 6, 7 or 8 minutes. In other embodiments, the maximum signal may be produced in about 5, 10, 15, 20, 25, 30, 35, 40, or 45 minutes.

(a) Detection Methods

In one embodiment, the molecular biosensors may be utilized for the detection of a target. The method generally involves contacting a molecular biosensor of the invention with the target. To detect a target, the method typically involves target-molecule induced co-association of two epitope-binding agents (present on the molecular biosensor of the invention) that each recognize the same repeating epitope on the target. The epitope-binding agents each comprise complementary signaling oligonucleotides that are labeled with detection means and are attached to the epitope binding agents through a flexible linker. Co-association of the two epitope-binding agents with the target results in bringing the two signaling oligonucleotides into proximity such that a detectable signal is produced. Typically, the detectable signal is produced by any of the detection means known in the art or as described herein.

In one particular embodiment, a method for the detection of a target that is a protein or polypeptide is provided. The protein or polypeptide comprises a repeating epitope. The method generally involves detecting a protein or polypeptide in a sample comprising the steps of contacting a sample with a molecular biosensor of the invention.

In another embodiment, the molecular biosensors may be used to detect a target that is a macromolecular complex in a sample. In this embodiment, the repeating epitope is preferably on each component of the macromolecular complex, such that when the complex is formed, the epitope-binding agents that recognize the repeating epitope are bought into proximity, resulting in the stable interaction of the first signaling oligo and the second signaling oligo to produce a detectable signal, as described above.

(b) Solid Surfaces

Optionally, the invention also encompasses a solid surface having one or more of the the molecular constructs of the invention attached thereto. Non-limiting examples of suitable surfaces include microtitre plates, test tubes, beads, resins and other polymers, as well as other surfaces either known in the art or described herein. In one embodiment, the solid surface comprises a nucleic acid sequence that is complementary to a signaling oligo of one or more molecular constructs, as described in the examples. Therefore, when the epitope binding agent recognizes the target comprising repeating epitopes, the signaling oligo of the molecular construct binds to the immobilized nucleic acid sequence. The binding may be detected by any means detailed above or in the examples.

In another embodiment the solid surface utilizes a three-component biosensor. In this embodiment, the oligonucleotide construct may be immobilized on a solid surface. The first epitope binding agent and second epitope binding agent are contacted with the surface comprising immobilized O and a sample that may comprise a target. In the presence of target, the first epitope binding agent, second epitope binding agent, and target bind to immobilized O to form a complex. Several methods may be utilized to detect the presence of the complex comprising target. The method may include detecting a probe attached to the epitope-binding agents after washing out the unbound components. Alternatively, several surface specific real-time detection methods may be employed, including but not limited to surface plasmon resonance (SPR) or total internal reflection fluorescence (TIRF).

The oligonucleotide construct, O, may be immobilized to several types of suitable surfaces. The surface may be a material that may be modified to contain discrete individual sites appropriate for the attachment or association of the three-component biosensor and is amenable to at least one detection method. Non-limiting examples of surface materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the surface may also vary without departing from the scope of the invention. A surface may be planar, a surface may be a well, i.e. a 364 well plate, or alternatively, a surface may be a bead or a slide.

The oligonucleotide construct, O, may be attached to the surface in a wide variety of ways, as will be appreciated by those in the art. O, for example, may either be synthesized first, with subsequent attachment to the surface, or may be directly synthesized on the surface. The surface and O may be derivatized with chemical functional groups for subsequent attachment of the two. For example, the surface may be derivatized with a chemical functional group including, but not limited to, amino groups, carboxyl groups, oxo groups or thiol groups. Using these functional groups, the O may be attached using functional groups either directly or indirectly using linkers. Alternatively, O may also be attached to the surface non-covalently. For example, a biotinylated O can be prepared, which may bind to surfaces covalently coated with streptavidin, resulting in attachment. Alternatively, O may be synthesized on the surface using techniques such as photopolymerization and photolithography. Additional methods of attaching O to a surface and methods of synthesizing O on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

(c) Use of Biosensors with No Detection Means

Alternatively, in certain embodiments it is contemplated that the molecular biosensor may not include a detections means. By way of example, when the molecular biosensor is a bivalent antibody construct, the bivalent antibody construct may not have labels for detection. It is envisioned that these alternative bivalent constructs may be used much like antibodies to detect molecules, bind molecules, purify molecules (as in a column or pull-down type of procedure), block molecular interactions, facilitate or stabilize molecular interactions, or confer passive immunity to an organism. It is further envisioned that the bivalent antibody construct can be used for therapeutic purposes. This invention enables the skilled artisan to build several combinations of antibodies that recognize any repeating epitope from any number of molecules into a bivalent, trivalent, or other multivalent aptamer construct to pull together those disparate molecules to test the effect or to produce a desired therapeutic outcome.

(d) Kits

In another embodiment, the invention is directed to a kit comprising a first epitope binding agent, to which is attached a first label, and a second epitope binding agent, to which is attached a second label, wherein (a) when the first epitope binding agent and the second epitope binding agent bind to a repeating epitope of the polypeptide, (b) the first label and the second label interact to produce a detectable signal. In a preferred embodiment the epitope-binding agent is an antibody construct, which comprises an antibody, a label and a signaling oligo. However, the epitope-binding agent may be an antibody fragment, an aptamer, or a peptide. The kit is useful in the detection of targets comprising a repeating epitope, and as such, may be used in research or medical/veterinary diagnostics applications. In particular, the kit may be used to detect microbial organisms, such as bacteria, viruses, and fungi.

(e) Diagnostics

In yet another embodiment, the invention is directed to a method of diagnosing a disease comprising the steps of (a) obtaining a sample from a patient, (b) contacting the sample with a first epitope binding agent construct and a second epitope binding agent construct, and (c) detecting the presence of a polypeptide, microbial organism, or macromolecular complex in the sample using a detection method, wherein the presence of the polypeptide, microbial organism, or macromolecular complex in the sample indicates whether a disease is present in the patient. In a one embodiment, (a) the first epitope binding agent construct is a first antibody to which a first label and a first signaling oligo are attached, (b) the second epitope binding agent construct is a second antibody to which a second label and a second signaling oligo, which is complementary to the first signaling oligo, are attached, and (c) the detection method is a fluorescence detection method, wherein, (d) when the first antibody binds to the polypeptide and the second antibody binds to the polypeptide, (e) the first signaling oligo and the second signaling oligo associate with each other, and (f) the first label is brought into proximity to the second label such that a change in fluorescence occurs.

In another embodiment, (a) the first epitope binding agent construct is a first peptide to which a first label and a first signaling oligo are attached, (b) the second epitope binding agent construct is a second peptide to which a second label and a second signaling oligo, which is complementary to the first signaling oligo, are attached, and (c) the detection method is a fluorescence detection method, wherein, (d) when the first peptide binds to the polypeptide and the second peptide binds to the polypeptide, (e) the first signaling oligo and the second signaling oligo associate with each other, and (f) the first label is brought into proximity to the second label such that a change in fluorescence occurs.

In other embodiments, the first epitope binding agent and the second epitope-binding agents are different types of epitope binding agents (i.e. an antibody and a peptide, an aptamer and an antibody, etc.). Preferred samples include blood, urine, ascites, cells and tissue samples/biopsies. Preferred patients include humans, farm animals and companion animals.

In yet another embodiment, the invention is directed to a method of screening a sample for targets comprising the steps of (a) contacting a sample with a first epitope binding agent construct and a second epitope binding agent construct, and (b) detecting the presence of a target in the sample using a detection method. Preferred targets include a polypeptide, which comprises a repeating epitope, and a microbial organism. In one embodiment, (a) the first epitope binding agent is a first antibody to which a first label and a first signaling oligo are attached, (b) the second epitope binding agent is a second antibody to which a second label and a second signaling oligo, which is complementary to the first signaling oligo, are attached, and (c) the detection method is a fluorescence detection method, wherein, (d) when the first antibody binds to the polypeptide and the second antibody binds to the polypeptide, (e) the first signaling oligo and the second signaling oligo associate with each other, and (f) the first label is brought into proximity to the second label such that a change in fluorescence occurs.

In another embodiment, (a) the first epitope binding agent is a first peptide to which a first label and a first signaling oligo are attached, (b) the second epitope binding agent is a second peptide to which a second label and a second signaling oligo, which is complementary to the first signaling oligo, are attached, and (c) the detection method is a fluorescence detection method, wherein, (d) when the first peptide binds to the polypeptide and the second peptide binds to the polypeptide, (e) the first signaling oligo and the second signaling oligo associate with each other, and (f) the first label is brought into proximity to the second label such that a change in fluorescence occurs.

In other embodiments, the first epitope binding agent and the second epitope-binding agents are different types of epitope binding agents (i.e. an antibody and a peptide, an aptamer and an antibody, etc.).

Definitions

The term "antibody" generally means a polypeptide or protein that recognizes and can bind to an epitope of an antigen. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, humanized antibodies, and a peptide comprising a hypervariable region of an antibody.

The term "aptamer" refers to a polynucleotide, generally a RNA or a DNA that has a useful biological activity in terms of biochemical activity, molecular recognition or binding attributes. Usually, an aptamer has a molecular activity such as binding to a target at a specific epitope (region). It is generally accepted that an aptamer, which is specific in its binding to any polypeptide, may be synthesized and/or identified by in vitro evolution methods.

As used herein, "detection method" means any of several methods known in the art to detect a molecular interaction event. The phrase "detectable signal", as used herein, is essentially equivalent to "detection method." Detection methods include detecting changes in mass (e.g., plasmin resonance), changes in fluorescence (e.g., FRET, FCCS, fluorescence quenching or increasing fluorescence, fluorescence polarization, flow cytometry), enzymatic activity (e.g., depletion of substrate or formation of a product, such as a detectable dye—NBT-BCIP system of alkaline phosphatase is an example), changes in chemiluminescence or scintillation (e.g., scintillation proximity assay, luminescence resonance energy transfer, bioluminescence resonance energy transfer and the like), and ground-state complex formation, excimer formation, colorimetric substance detection, phosphorescence, electro-chemical changes, and redox potential changes.

The term "epitope" refers generally to a particular region of a target. Examples include an antigen, a hapten, a molecule, a polymer, a prion, a microbe, a cell, a peptide, polypeptide, protein, a ligand, a receptor, or macromolecular complex. An epitope may consist of a small peptide derived from a larger polypeptide. An epitope may be a two or three-dimensional surface or surface feature of a polypeptide, protein or macromolecular complex that comprises several non-contiguous peptide stretches or amino acid groups.

The term "epitope binding agent" refers to a substance that is capable of binding to a specific epitope of an antigen, a polypeptide, a protein or a macromolecular complex. Non-limiting examples of epitope binding agents may include aptamers, double-stranded DNA sequence, ligands and fragments of ligands, receptors and fragments of receptors, antibodies and fragments of antibodies, polynucleotides, coenzymes, coregulators, allosteric molecules, and ions.

The term "epitope binding agent construct" refers to a construct that contains an epitope-binding agent and can serve in a "molecular biosensor" with another molecular biosensor. Preferably, an epitope binding agent construct also contains a "linker," and a "signaling oligo". Epitope binding agent constructs can be used to initiate the aptamer selection methods of the invention. A first epitope binding agent construct and a second epitope binding agent construct may be joined together by a "linker" to form a "bivalent epitope binding agent construct." An epitope binding agent construct can also be referred to as a molecular recognition construct. An aptamer construct is a special kind of epitope binding agent construct wherein the epitope binding agent is an aptamer.

The term "label", as used herein, refers to any substance attachable to a polynucleotide, polypeptide, aptamer, nucleic acid component, or other substrate material, in which the substance is detectable by a detection method. Non-limiting examples of labels applicable to this invention include but are not limited to luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

As used herein, the term "macromolecular complex" refers to a composition of matter comprising a macromolecule. Preferably, these are complexes of one or more macromolecules, such as polypeptides, lipids, carbohydrates, nucleic acids, natural or artificial polymers and the like, in association with each other. The association may involve covalent or non-covalent interactions between components of the macromolecular complex. Macromolecular complexes may be relatively simple, such as a ligand bound polypeptide, relatively complex, such as a lipid raft, or very complex, such as a cell surface, virus, bacteria, spore and the like. Macromolecular complexes may be biological or non-biological in nature.

The term "molecular biosensor" and "molecular beacon" are used interchangeably herein to refer to a construct comprised of at least two epitope binding agent constructs. The molecular biosensor can be used for detecting or quantifying the presence of a target using a chemical-based system for detecting or quantifying the presence of an analyte, a prion, a protein, a nucleic acid, a lipid, a carbohydrate, a biomolecule, a macromolecular complex, a fungus, a microbial organism, or a macromolecular complex comprised of biomolecules using a measurable read-out system as the detection method.

The term "signaling oligo" means a short (generally 2 to 15 nucleotides, preferably 5 to 7 nucleotides in length) single-stranded polynucleotide. Signaling oligos are typically used in pairs comprising a first signaling oligo and a second signaling oligo. Preferably, the first signaling oligo sequence is complementary to the second signaling oligo. Preferably, the first signaling oligo and the second signaling oligo can not form a stable association with each other through hydrogen bonding unless the first and second signaling oligos are brought into close proximity to each other through the mediation of a third party agent.

EXAMPLES

The following examples illustrate various iterations of the invention.

Example 1

General Biosensor Design

The overall design of molecular biosensors is illustrated in FIG. 1. This concept is derived from molecular beacons for detecting DNA binding proteins and from aptamer-based molecular beacons for detecting proteins that were previously developed [12-15]. A pair of antibodies recognizing non-overlapping epitopes of the protein is labeled with a pair of short complementary signaling oligonucleotides using a long flexible PEG-based crosslinker, respectively. Oligonucleotides are modified with a pair of fluorophores that may function as a donor and an acceptor in Fluorescence Resonance Energy Transfer (FRET) [16]. In the presence of the target protein both antibodies will bind to the target resulting in a great increase of the local concentration of signaling oligonucleotides. This in turn will lead to annealing of the oligonucleotides bringing the fluorophores to close proximity resulting in efficient FRET that can be used as a signal for target protein detection. Recent quantitative analysis of binding properties of the ligands containing long flexible linkers indicated that linkers with the lengths of tens of nanometers should be compatible with the design illustrated in FIG. 1A. Such long linkers should allow enough of room and flexibility for effective formation of complexes containing two antibodies and even very large protein.

Figure 1B:
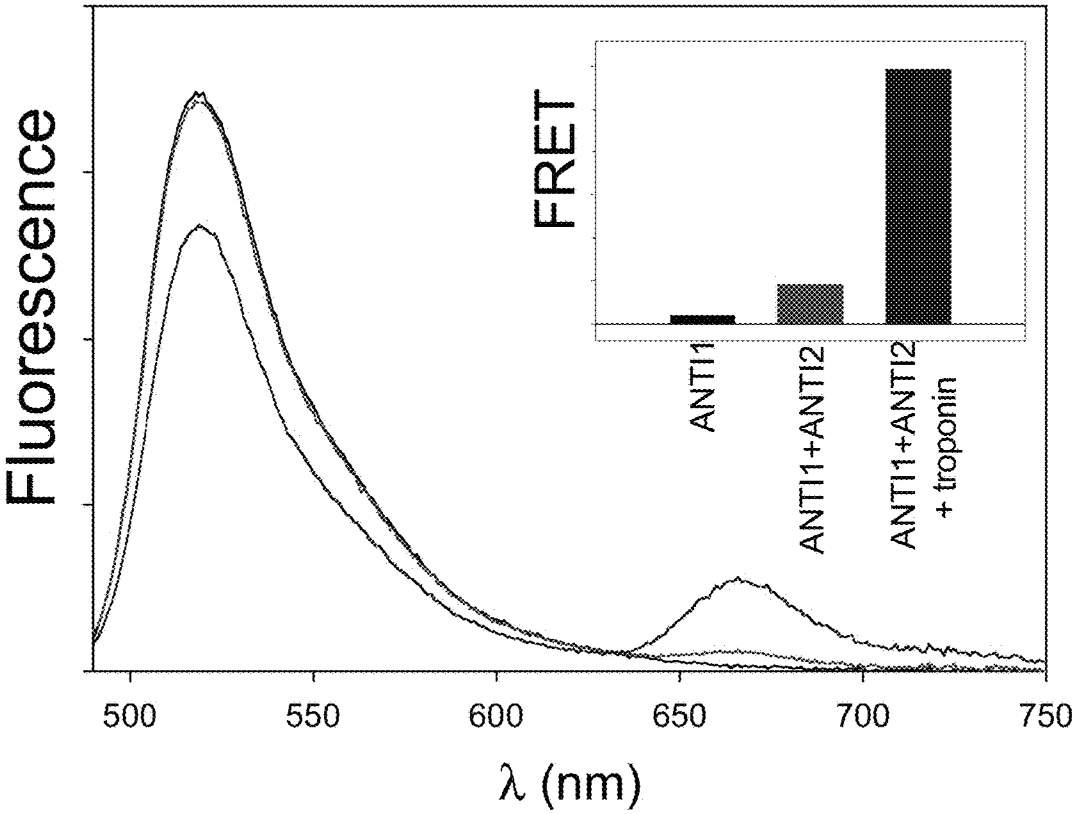
(FIG. 1B) Proof-of-principle for molecular biosensors. Black line: emission spectrum of 20 nM ANTI1 labeled with fluorescein. Red line: Emission spectrum of a mixture of 20 nM ANTI1 and 25 nM ANTI2 labeled with Cy5. Blue line: 20 nM ANTI1 and 25 nM ANTI2 in the presence of 20 nM human cardiac troponin I. Excitation was at 490 nm. Inset: FRET signals for each sample (emission at 670 nm with the excitation at 490 nm).
Figure 1C:
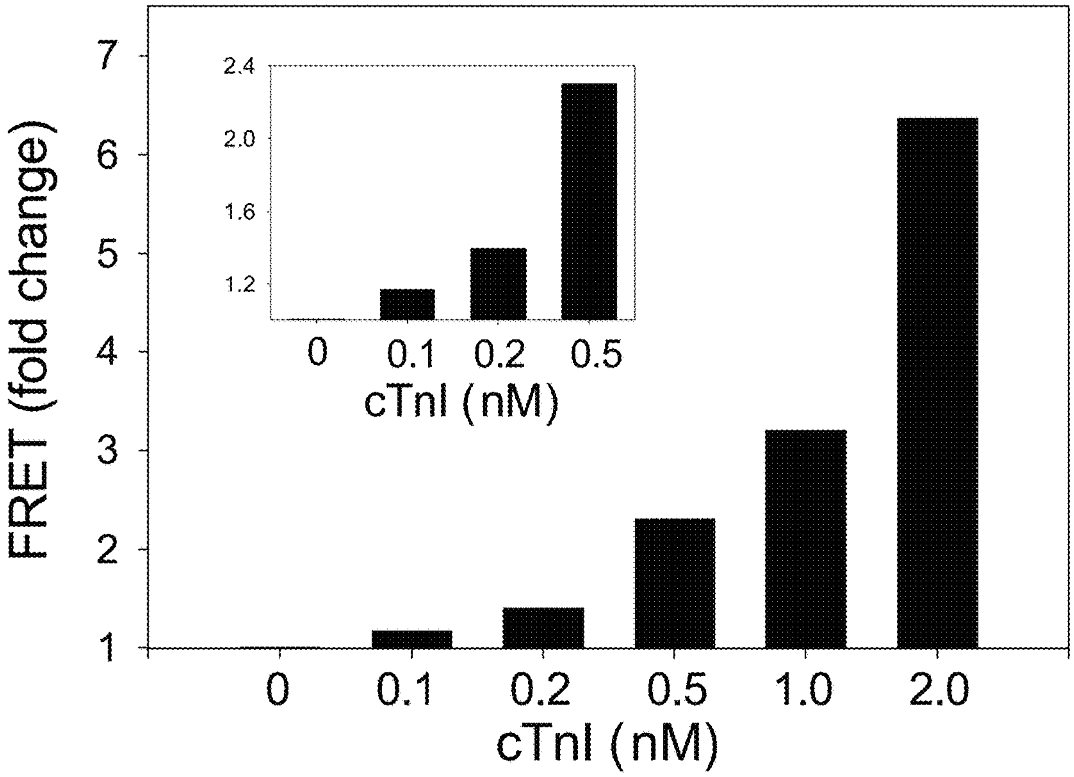
(FIG. 1C) Cardiac troponin sensor response at low concentrations of the protein.

Cardiac troponin I has been used as a target protein to demonstrate feasibility of the sensors depicted in FIG. 1A. When the labeled antibodies were mixed in the absence of cardiac troponin, no significant FRET signal was observed when fluorescence spectra of donor-labeled antibody in the absence and the presence of acceptor-labeled antibody were compared (FIG. 1B). Upon addition of troponin, a large FRET signal was observed illustrated by several fold increase of emission at 670 nm with the excitation at 490 nm and quenching of donor emission at 520 nm. This signal allowed very sensitive (down to ~40 μM troponin) detection of the protein (FIG. 1C). Specificity of the sensor for cardiac troponin was tested. No FRET signal was observed when nonspecific related control protein (porcine muscle troponin) was added to the sensor whereas a robust response with cardiac troponin was observed. Also, unlabeled cardiac troponin antibodies acted as competitors in the molecular biosensor assay indicating that the signal generated by the molecular biosensor in the presence of troponin was due to specific interactions between labeled antibodies and the protein. High specificity of molecular biosensor is expected due to the necessary coincidence of three molecular events (the recognition of the target protein by each of the two antibodies and the association of the complementary signaling oligonucleotides) for generating signal in the presence of the target. In the absence of any one of these, the sensor will generate no signal. Generality of the sensor design has been confirmed by using the same blueprint as used in the case of troponin for preparing a successful sensor for other targets (C-reactive protein, insulin, C-peptide).

Example 2

Antibody-Based Biosensors for Detecting Bacteria

Figure 2:
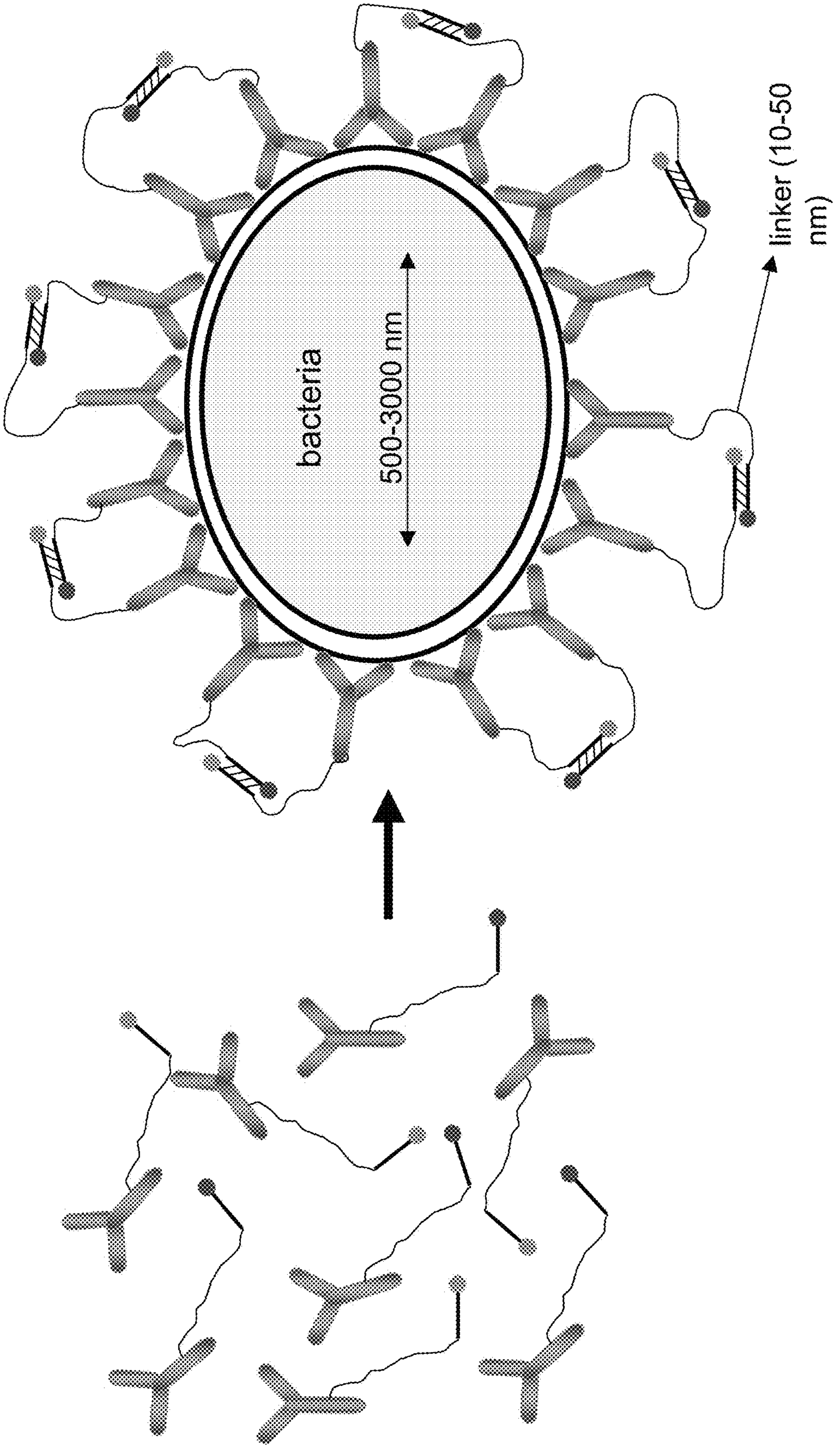
FIG. 2 depicts the design of antibody-based sensor for detecting pathogens.
Figure 3A:
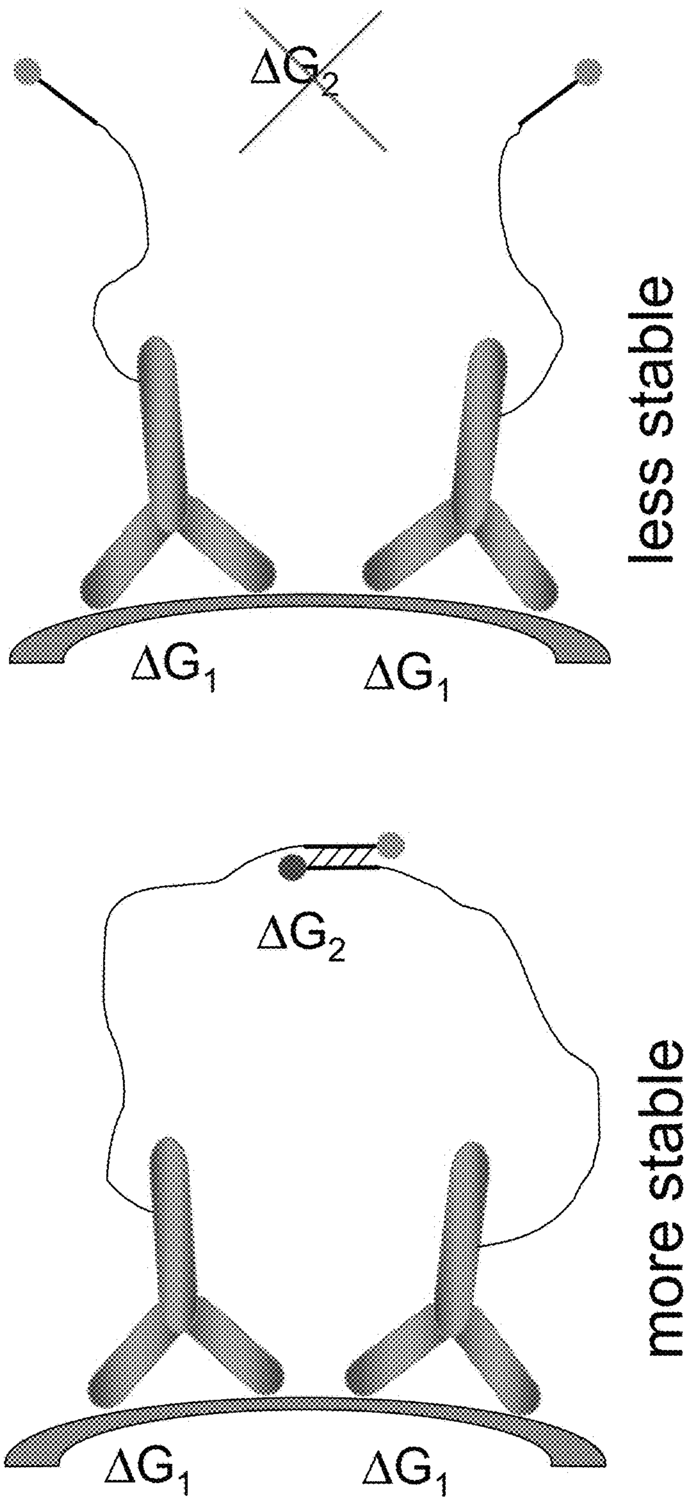
FIG. 3A depicts the mechanism of preferential binding of the antibodies labeled with complementary signaling oligonucleotides next to each other.

By analogy to the target-protein induced annealing of signaling oligonucleotides (FIG. 1), it was hypothesized that a similar effect could be produced by binding of signaling oligonucleotide-labeled antibodies to the repeating epitopes on a surface of a bacterial cell (FIG. 2). Taking into account the dimensions of the bacterial cell (~500-~3000 nm) and the length of flexible linkers used to attach the oligonucleotides to the antibodies (10-50 nm), it was expected that even a moderate density of cell surface epitopes recognized by the antibody should be sufficient to bring the antibodies into the proximity that would allow annealing of the signaling oligonucleotides. This would in turn bring the donor and acceptor fluorochromes into the proximity to produce FRET signal in the presence of target cells. It would seem that similar to the molecular biosensor sensors for protein targets (FIG. 1) it would be necessary to have two antibodies (labeled with complementary signaling oligonucleotides, respectively) to two distinct cell surface epitopes for the assay depicted in FIG. 2 to work. However, it was hypothesized that it would be sufficient to use a mixture of the same antibody labeled with two complementary signaling oligonucleotides, respectively. The reasons for that are illustrated in FIG. 3A. Complementary oligonucleotides provide additional favorable binding energy when the antibodies labeled with complementary oligonucleotides bind next to each other. This energy is absent when the two neighboring antibodies are labeled with the same signaling oligonucleotide (an arrangement that does not generate FRET signal). Thus, when a mixture of the same antibody labeled with two complementary signaling oligonucleotides is used, the design has a built-in selection process whereby the antibodies capable of producing FRET signal will be preferentially bound near each other. The preliminary data described below has fully validated the design illustrated in FIG. 2.

Example 3

*E. coli* Biosensors

To obtain proof-of-principle evidence validating the design illustrated in FIGS. 2 and 3A, a series of experiments was performed using *E. coli* 0157:H7 as detection targets. Affinity-purified goat polyclonal antibodies specific for *E. coli* 0157:H7 were obtained from KPL. Two samples of signaling oligonucleotide-labeled antibodies were prepared for each of the above antibodies. One was modified (via a long flexible linker) with a 5'-fluorescein-GCTCAT and the other was modified with a Cy5-modified complementary signaling oligonucleotide (5'-Cy5-ATGAGC). All fluorescence measurements were done using Analyst AD fluorescence plate reader (Molecular Devices, Sunnyvale, Calif.).

Figure 3B:
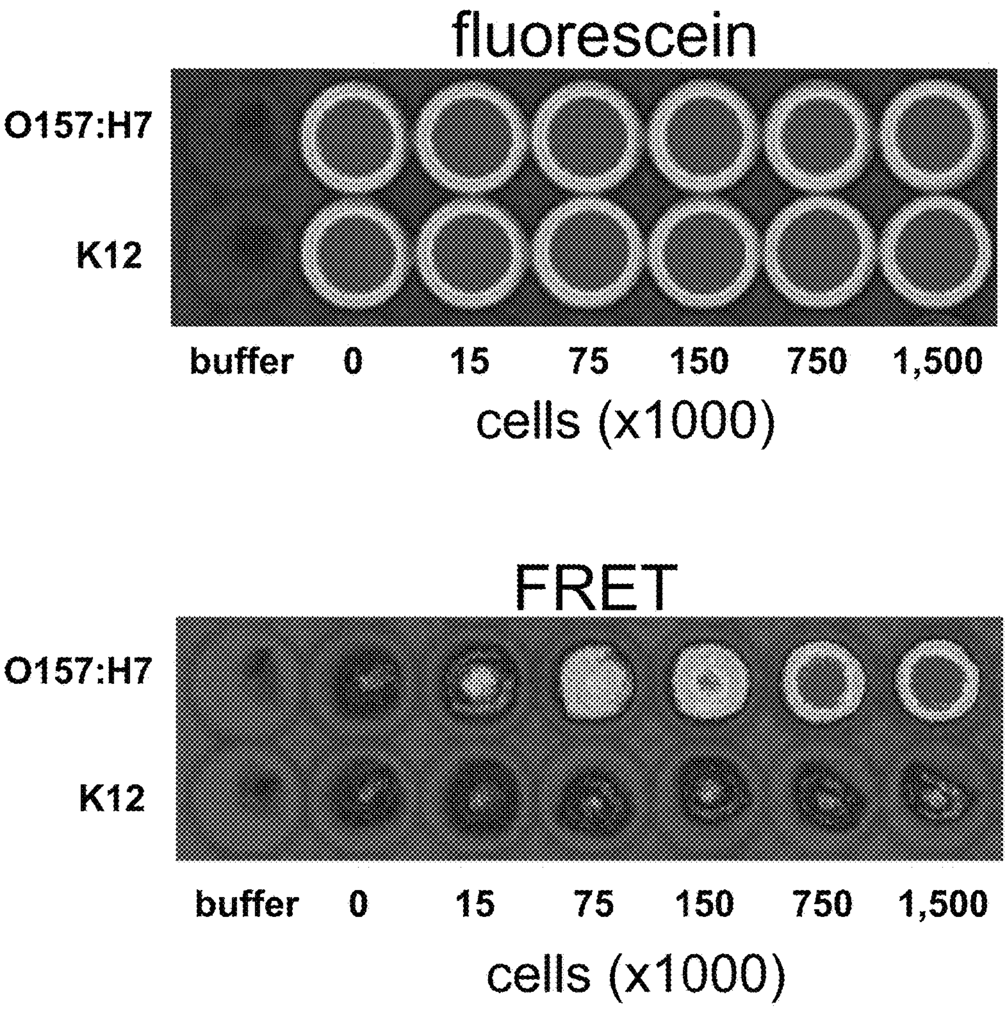
(FIG. 3B) Proof-of-principle experiment demonstrating feasibility of the sensor design illustrated in FIG. 2. False-color fluorescence images of the wells of the 96-well microplate containing equimolar mixture of labeled antibodies incubated with indicated amounts of target cells (O157:H7) or negative control cells (K12) are shown. Top panel is the image of the emission at 520 nm (excited at 488 nm) and the bottom panel is the image of emission at 670 nm (excited at 488 nm).
Figure 4:
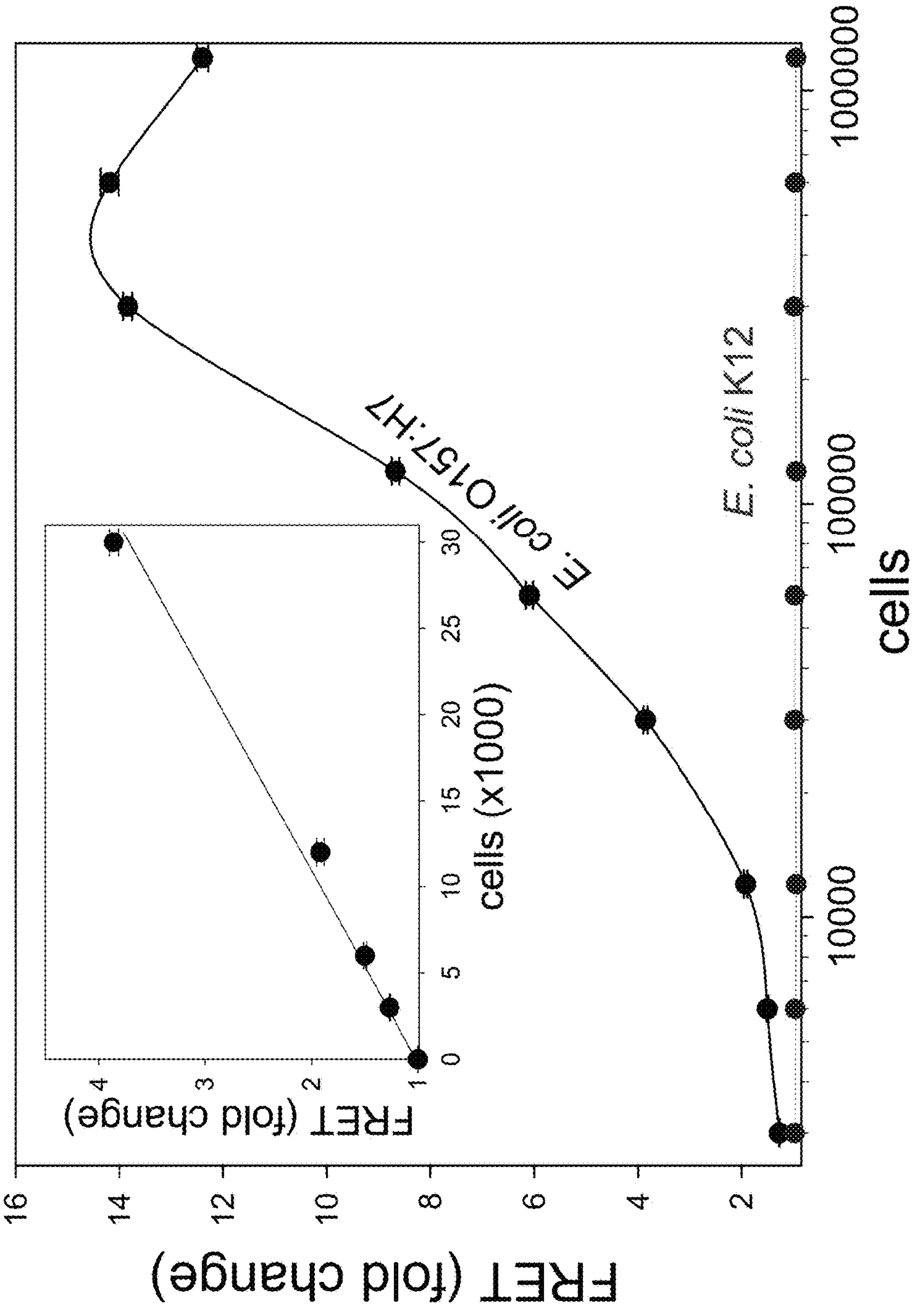
FIG. 4 depicts FRET signal produced by the 20 nM/25 nM mixture of antibodies labeled with fluorescein and Cy5-modified complementary signaling oligonucleotides at indicated amounts of cells (in 20 ml assay, 384-well microplate). Averages and standard deviations of 3 independent measurements are shown. Black symbols: *E. coli* O157:H7; blue symbols: *E. coli* K12.

When a mixture of *E. coli* 0157:H7 labeled antibodies was incubated with increasing amounts of *E. coli* 0157:H7 cells, a large dose-dependent FRET signal (emission at 670 nm with the excitation at 488 nm) was observed (FIG. 3B). In contrast, no FRET signal was recorded when the same amounts of *E. coli* K12 cells were used demonstrating specificity of the sensor. FIG. 4 shows the results of the three independent repeats of the assay performed at a wide range of target cells amounts. Few thousands of target cells were easily detectable using these assay conditions with high reproducibility (mean CV was 1.7%; range: 0.7-3.9%). No signal with negative control (*E. coli* K12) has been detected at any amount of the cells tested. At very high amounts of the target cells, the FRET signal started to decrease most likely due to the decrease in the average amount of antibodies bound to each cell due to the depletion of the free antibody in the reaction mixture. Data shown in FIG. 3A and FIG. 4 demonstrate the feasibility of the assay design illustrated in FIG. 2.

Figure 5:
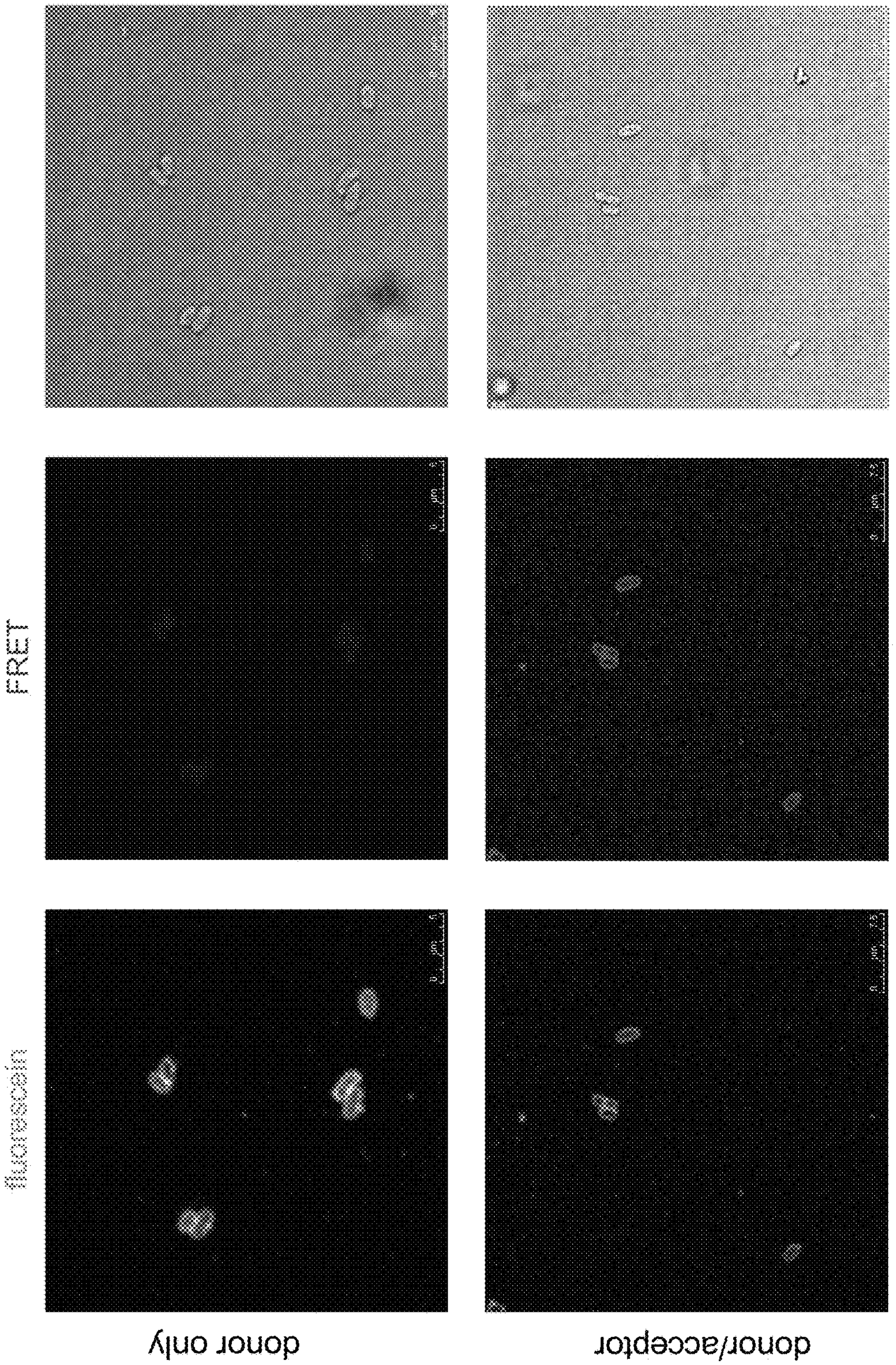
FIG. 5 depicts fluorescence confocal microscope images of the *E. coli* O157:H7 cells incubated with the antibody labeled with fluorescein-modified signaling oligonucleotide (donor only) or with the mixture of antibody labeled with fluorescein and Cy5-modified complementary oligonucleotides (donor/acceptor). Fluorescein image was taken with excitation at 488 nm and emission at 520 nm. FRET image was taken with excitation at 488 nm and emission at 670 nm.

The assay design illustrated in FIG. 2 assumes that FRET signal is generated by annealing of complementary oligonucleotides attached to the antibodies co-binding to the same cell. The other possibility could be that the FRET signal could be produced by annealing of signaling oligonucleotides attached to the antibodies bound to different cells (i.e. resulting in antibody-induced aggregation of the cells). To investigate the nature of the FRET signal generated in the presence of the target cells, we have obtained confocal microscope images of *E. coli* 0157:H7 cells incubated with the mixture of antibody labeled with fluorescein and Cy5-modified complementary oligonucleotides (FIG. 5; donor/acceptor) and the same cells incubated only with the antibody labeled with fluorescein-modified signaling oligonucleotide that lacks the ability of crosslinking via annealing of the complementary oligonucleotides (FIG. 5; donor only). In both cases individual cells and cells aggregates could be found. No increase in cell aggregation was detected in donor/acceptor sample compared to donor-only sample arguing against annealing of signaling oligonucleotides between different cells as a mechanism for FRET signal. Furthermore, large FRET signal could be seen within the individual cells (FIG. 5, bottom FRET panel). These observations indicate that the major route for the FRET signal produced in the presence of target cells is the process schematically illustrated in FIG. 2.

Example 4

Biosensor Response Time

Figure 6:
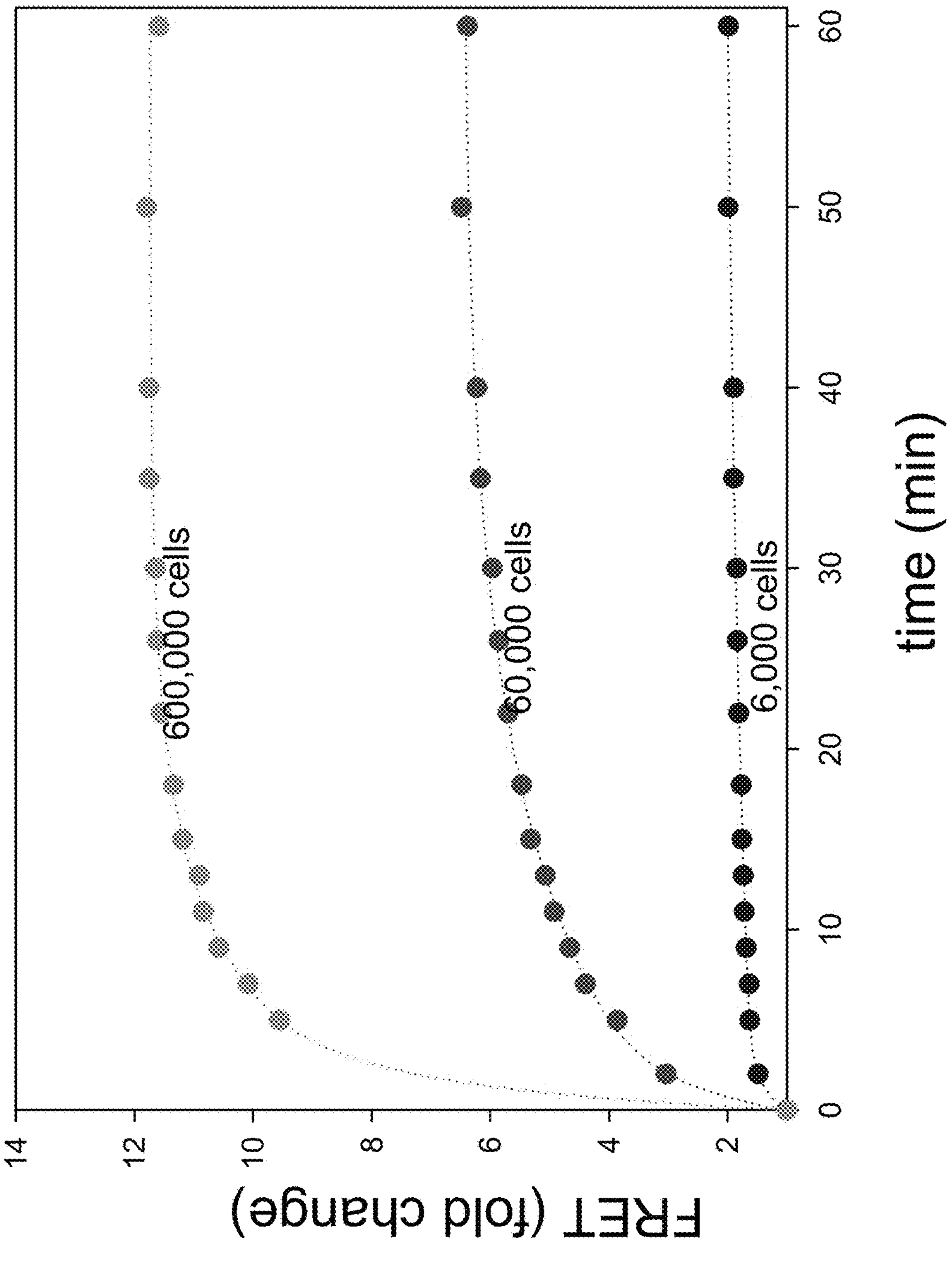
FIG. 6 depicts the kinetics of the biosensor response. Indicated amounts of *E. coli* O157:H7 cells were added to 20 nM mixture of antibody labeled with fluorescein and Cy5-modified complementary oligonucleotides and FRET signal (emission at 670 nm with excitation at 488 nm) was monitored over time.

One of the important advantages of the sensor design illustrated in FIG. 2 is the uncomplicated rapid manner by which the assay can be performed. Thus, in the next experiment the response time of the sensor is determined. Various amounts of target cells were added to the mixture of antibody labeled with fluorescein and Cy5-modified complementary oligonucleotides and the FRET signal was monitored as a function of incubation time (FIG. 6). Maximum FRET signal was obtained after ~30 min incubation. After ~5 min incubation >80% of the maximal FRET signal was produced (thus, if necessary, it would be possible to perform the assay with 5 min incubation). These data confirm the rapid response time the biosensor.

Example 5

Sensitivity

Figure 7:
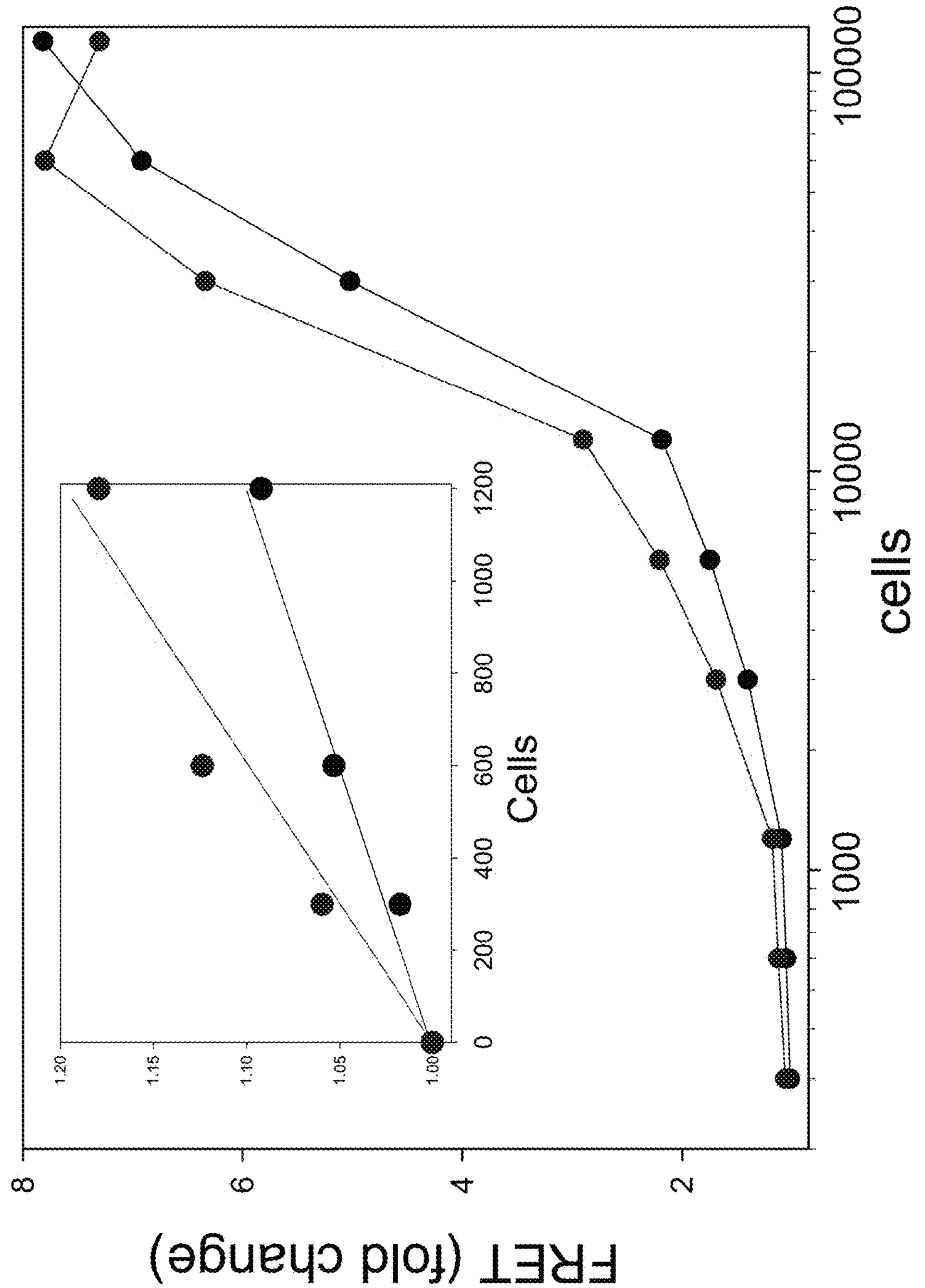
FIG. 7 depicts the increased sensitivity of target cell detection at lower antibody concentration. Black symbols: 10/12 nM nM antibody mixture; blue symbols: 5/6.2 nM nM antibody mixture.

Detection sensitivity will be one of the important parameters that will define the practical utility of the biosensors. One way to optimize assay sensitivity could be to find optimal concentrations of the antibodies. Reducing antibody concentrations could increase assay sensitivity since a bigger fraction of the total antibody concentration may be bound to cells at a given target cell density (provided that the antibody concentrations are not reduced below the Kd of antibody-antigen complex). FIG. 7 shows the response of the biosensor at two (lower) antibody concentrations. As expected, lowering antibody concentrations allowed detection of lower target cell amounts. It is estimated that using a 5/6.2 nM antibody mixture the sensitivity of detection was ~150 cells/20 ml assay.

Figure 8:
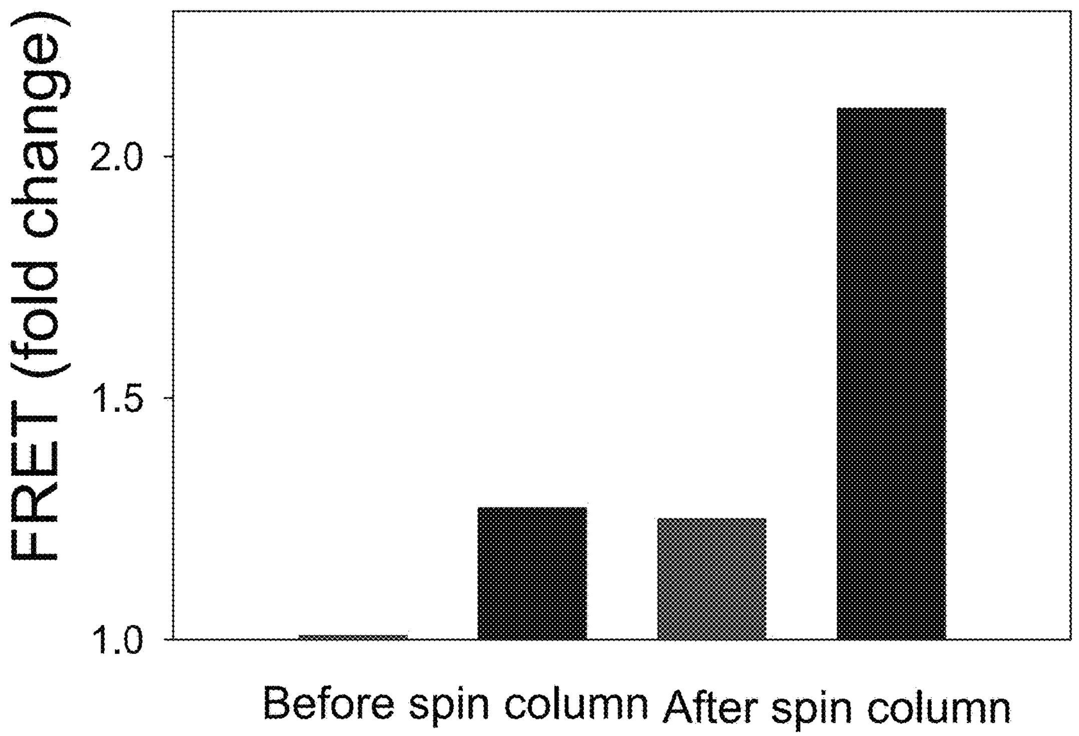
FIG. 8 depicts a sample concentration step that can be used to enhance detectabilty of low amounts of the bacteria. Red bars: 3000 cells/ml sample; blue bars: 300,000 cells/ml sample.

Methods for bacteria detection often employ some form of sample enrichment step to enhance detection of low cell amounts. A simple test was performed to demonstrate that such step can be added to the assay. Two diluted samples of *E. coli* 0157:H7 were prepared. One (3000 cells/ml; 60 cells/20 ml assay) was below the detection limit using a sensor employing 20/25 nM mix of labeled antibodies (FIG. 8). The other (300,000 cells/ml; 6000 cells/20 ml assay) gave relatively low signal with 20/25 nM mix of labeled antibodies (FIG. 8). Both samples were then concentrated ~10 fold by a quick spin on a spin column with a semipermeable membrane and were re-measured. After the spin column treatment, the sample that was previously undetectable produced easy to measure signal, whereas the signal for the more concentrated sample (that previously gave relatively low reading) was dramatically improved (FIG. 8).

Example 6

Biosensor to *Salmonella*

Figure 9:
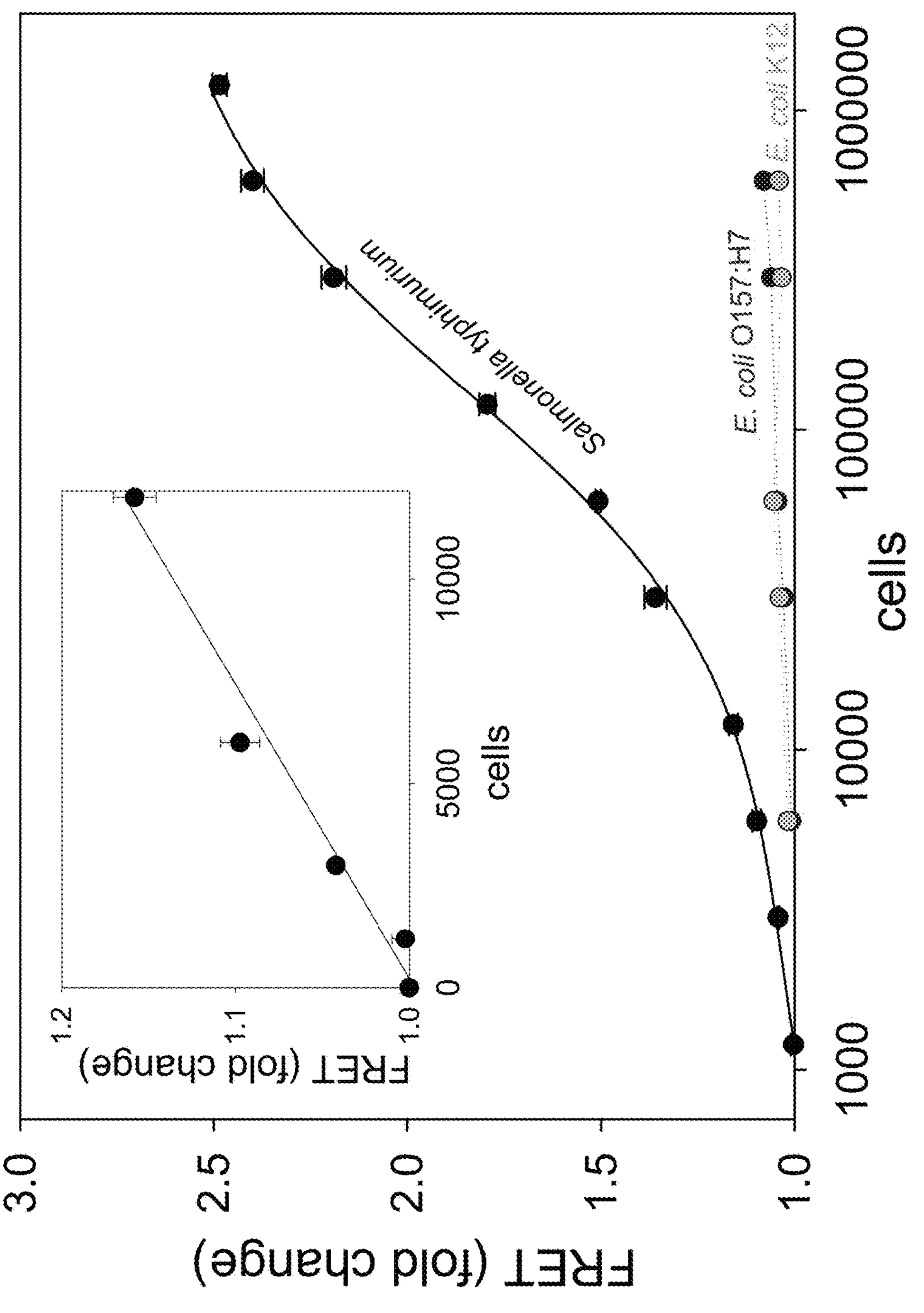
FIG. 9 depicts a biosensor for *Salmonella typhimurium*. FRET signal produced by the 20 nM/25 nM mixture of antibodies labeled with fluorescein and Cy5-modified complementary signaling oligonucleotides at indicated amounts of cells (in 20 μl assay, 384-well microplate). Averages and standard deviations of 3 independent measurements are shown. Black symbols: *Salmonella typhimurium*; cyan symbols: *E. coli* K12; blue symbols: *E. coli* O157:H7.
Figure 10:
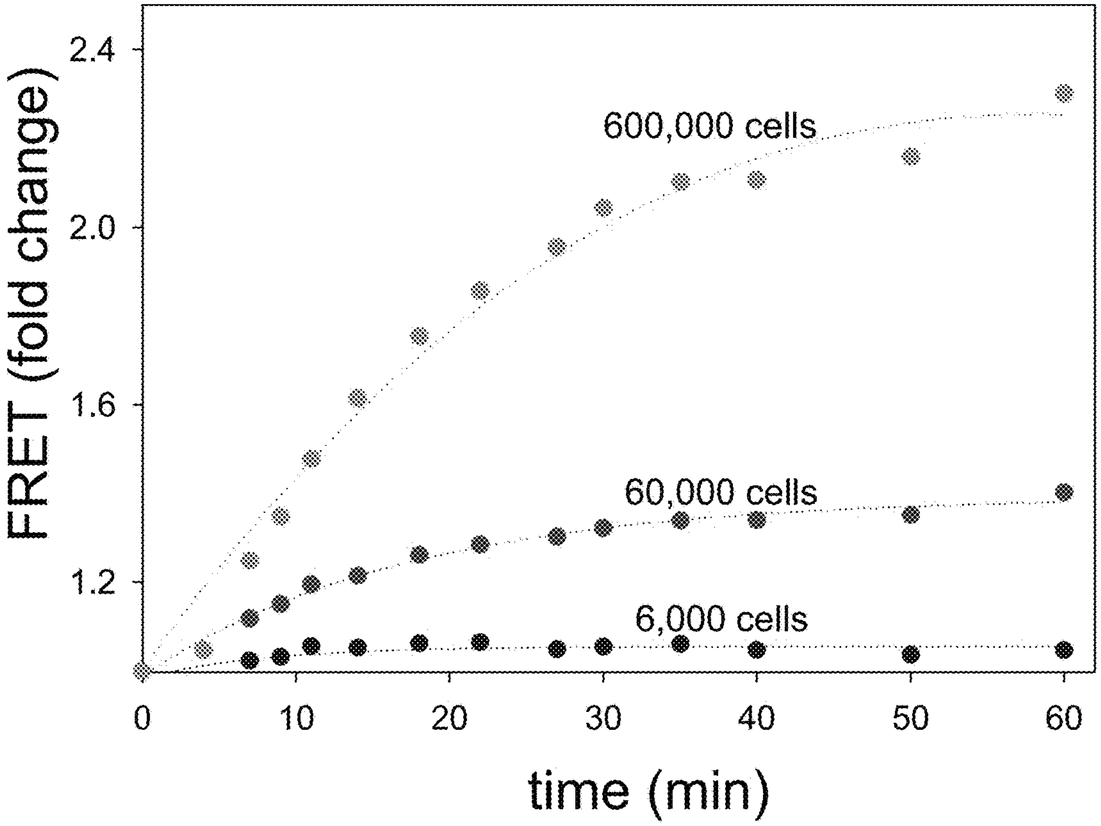
FIG. 10 depicts the kinetics of a *Salmonella typhimurium* biosensor response. Indicated amounts of *Salmonella* cells were added to 20 nM/25 nM mixture of antibody labeled with fluorescein and Cy5-modified complementary oligonucleotides and FRET signal (emission at 670 nm with excitation at 488 nm) was monitored over time.

In order to demonstrate the generality of the sensor design illustrated in FIG. 2, we used the same procedure as used in the case of *E. coli* O157:H7 sensor to prepare a sensor for a different bacteria (*Salmonella typhimurium*). FIG. 9 shows that as in the case of *E. coli* 0157:H7, a large dose-dependent FRET signal was observed with *Salmonella* cells. In contrast, very little FRET signal in the presence of *E. coli* K12 or *E. coli* O157:H7 was observed demonstrating the specificity of the sensor for the target cells. As in the case of *E. coli* O157:H7 reproducibility was excellent (mean CV was 1.0%; range: 0.3-2.2%). FRET signal in the case of *Salmonella* was smaller compared to *E. coli* O157:H7 most likely reflecting differences in properties of corresponding antibodies (for example, different surface density of the epitopes recognized by the antibodies). Nevertheless, the fact that the same design blueprint applied to two different bacteria cells produced functional sensors provides a strong indication of the generality of the design illustrated in FIG. 2. Kinetics of *Salmonella* sensor response (FIG. 10) was similar to that observed for *E. coli* O157:H7 sensor.

Example 7

Preparation of Antibodies with Linkers

Preparation of the antibodies modified with short oligonucleotides via long flexible linkers is an important step in preparing the biosensors for bacteria. A reliable procedure to label and purify the antibodies has been developed. Briefly, the antibody is treated with Traut's reagent to introduce free —SH groups. 5'-amino labeled oligonucleotide is reacted with NHS-maleimide bifunctional crosslinker producing maleimide-containing oligonucleotide that is reacted with —SH containing antibody. A long flexible linker is introduced to the oligonucleotide either during standard oligonucleotide synthesis [12] or can be a part of the bifunctional crosslinker. Labeled antibody is purified by FPLC size exclusion chromatography.

Evaluating the pros and cons of various sensor design variants will involve performing the assays with a series of samples containing a range of dilution of each of the bacterial targets. Performance of the sensor will be evaluated by determining signal-to-background ratios, sensitivity and specificity of the detection. Sensitivity will be defined as the lowest amount of the target producing a signal higher than 3×standard deviation over the background measured with no target. Specificity will be evaluated by comparing the signals measured in the presence of a given target with the signal measured at the same amount of unrelated bacteria.

Analysis of the properties of ligands with long flexible linkers indicated that the linkers with a length of up to 50 nm should produce a functional sensor when used to attach the oligonucleotides to the antibody. However, these conclusions are based on experiments performed in solution using a simple model system. It is not clear if these conclusions apply to our bacteria sensor design (FIG. 2) where the antibodies bind to a surface of micrometer-size cell. We will thus compare the performance of the assays using antibodies labeled with 10, 20, 30, 40 and 50 nm long linkers. Length of the linker can be manipulated using constructs in which the flexible linker is incorporated during standard oligonucleotide synthesis [12]. Various lengths of the linkers will be tried with all four bacterial targets since it might be possible that the optimal length of the linker could depend on the surface density of the antigens recognized by the antibodies. For example, in preliminary experiments we have observed that the FRET signal obtained in the case of *Salmonella* was significantly lower then in the case of *E. coli* O157:H7. It could be that the FRET signal in the case of *Salmonella* could be improved by using different length of the linker.

Example 8

Optimal Ratio of Oligonucleotide:Protein in Antibody-Oligonucleotide Conjugate

FIG. 2 schematically depicts antibodies labeled with one oligonucleotide per protein molecule. In reality, this does not need to be the case—it is unnecessary to prepare a homogenous preparation of such labeled antibodies. Degree of labeling of the antibodies can be modulated by changing the concentrations of the reagents and/or the time of coupling reactions. The performance of the sensors with antibodies labeled with oligonucleotides to a different degree (from ~1 to ~5 oligonucleotides per antibody) can be compared to find the optimal ratio.

Example 9

Optimal Length of the Signaling Oligonucleotide

The length of the oligonucleotides used to label the antibody will be important for optimal functioning of the sensors. To be more precise, it is not the length but the free energy change for their hybridization to the complementary strand that is the parameter of interest. If the binding affinity between the two complementary oligonucleotides used to label the antibody is too large, they will exhibit excessive target-independent association resulting in high background signal. If the affinity is too small, the background binding will be small but the target-induced annealing of the oligonucleotides will be reduced resulting in suboptimal FRET signal in the presence of target cells. In preliminary experiments, oligonucleotides with hybridization ΔG at 0.1 M NaCl of ~7.5 kcal/mole were used. While these oligonucleotides worked fine it is not known if they were optimal. The performance of the sensors utilizing the oligonucleotides with hybridization AG's in the range from 6 to 9 kcal/mole will therefore be tested to determine the optimal AG value for high signal in the presence of the target cells and low background in the absence of target.

Example 10

Dry-Chemistry Approach

To assure long-term stability, oligonucleotide-labeled antibodies have been stored frozen at −80°. When stored at 4°, they retain their functionality for at least 2 weeks. These observations demonstrate that the stability of the main component of the sensors is similar to any other immunological assay and is thus compatible with practical applications of the sensors. Homogenous assays in microplates can be greatly simplified by applying a dry-chemistry approach [17, 18]. In this approach the assay mixture solution is dried into the wells of the microplate. If the assay reagents are compatible with this procedure, the assay is simplified since it requires only a simple addition of the sample solution to a microplate well with the dried assay components. The shelf life of the assay can be increased and the storage requirements simplified when dry-chemistry approach is applied.

Thus, the performance of the sensors will be tested using a dry-chemistry approach. The sensor mixtures (5 ml labeled antibody solution in a buffer containing 5% sorbitol which was shown to facilitate retention of functional properties of assay reagents after drying [18]) will be evaporated in the wells of 384-well microplate overnight in a desiccator over silica gel [17, 18]. The sensitivity of the assays for the four bacterial targets will be compared using the dry-chemistry assay with the assays performed using the "normal" wet chemistry approach. If no significant decrease of assay sensitivity due to drying and dissolution of the assay components are observed, the stability of the assay in dry-chemistry format will be further tested. The plates with dry assay components sealed with a plate sealing film will be stored at room temperature or at 4° for an extended period of time (24 weeks). The performance of the stored dry-chemistry assays will be evaluated in weekly intervals to determine the effect of time of storage and storage temperature on the assay performance.

Example 11

Improving Sensitivity

Sensitivity of target cell detection will define where and how the sensors can be ultimately used. Current sensitivity of the sensors as determined in the preliminary experiments is equal or better to ELISA assays for bacteria detection [2]. Thus, even before any optimization of these sensors has been performed, they appear to be a superior alternative to standard ELISA assays since they offer the same sensitivity but the results can be obtained in a fraction of time required to perform ELISA and they are vastly simpler to perform. For the detection of the amounts of cells below the current sensitivity limit, the sample potentially could be enriched using semipermeable membrane concentration step (as illustrated by preliminary data illustrated by FIG. 8) or an cell culture enrichment step could be performed. Nevertheless, the more sensitive the sensors will be, the more applications they could potentially find. The following ideas for improving assay sensitivity may thus be tested:

(i) Alternative FRET Probes. One relatively straightforward approach to improve sensor sensitivity will be to use better fluorescence probes (probes with increased brightness). It will be tested if replacing the fluorescein-Cy5 donor-acceptor pair used in all preliminary experiments with a brighter and more photostable pair of probes (Alexa488/Alexa647 or Alexa546/Alexa647) can produce an increase in sensitivity.

(ii) Time-Resolved FRET (LRET). Another potential approach to increase FRET based assay sensitivity is to increase signal-to-background ratio of FRET signal. Majority of background signal in FRET-based assays originates from the spillover of the donor emission to the acceptor detection channel and from direct excitation of the acceptor at donor excitation wavelength. These two sources of the elevated background (as well as the background due to light scattering) can be effectively removed by employing Luminescence Energy Transfer (LRET) using lanthanide chelates as donor labels [19-23]. These labels exhibit very long (hundreds of microseconds) fluorescence lifetimes allowing the employment of pulsed excitation and delayed gated emission measurements that have been shown to dramatically reduce background signals in FRET-based homogenous assays [19, 22]. LRET is also very effective in removing the background due to light scattering or due to fluorescent impurities in the sample. This could be beneficial when turbid or autofluorescent samples need to be analyzed. For each of the four bacterial targets, antibodies labeled with complementary oligonucleotides modified with europium chelate and with Cy5, respectively, will be prepared. The performance of the sensors utilizing LRET-based detection will be compared with the sensors utilizing standard FRET detection.

Figure 11:
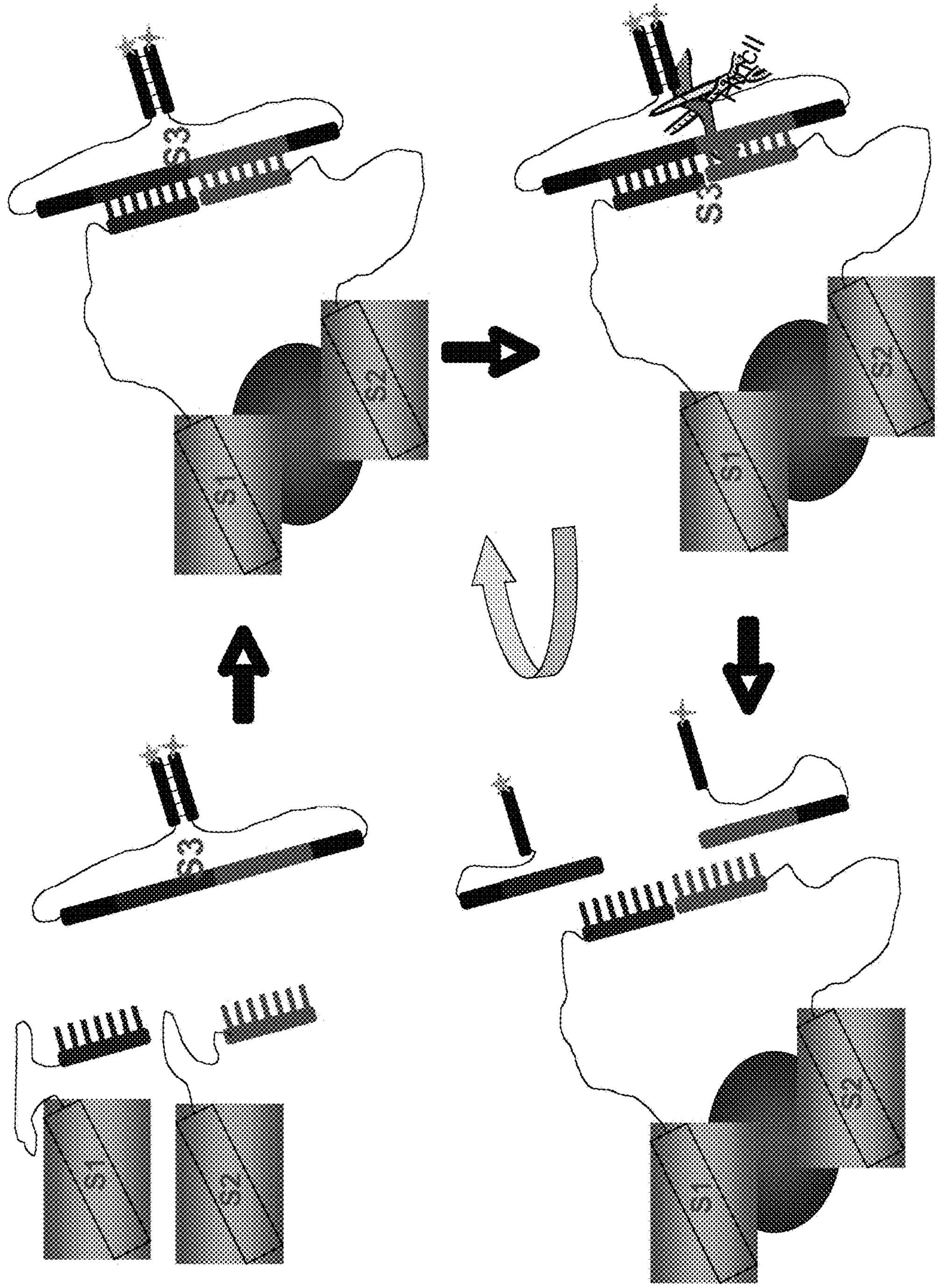
FIG. 11 depicts the homogenous restriction-enzyme based signal amplification methodology compatible with homogenous nature of molecular biosensors. S1 and S2 correspond to the antibodies recognizing the target labeled with short oligonucleotides complementary to the region of S3 flanking the restriction enzyme cleavage site in S3.

(iii) Restriction-Enzyme Based Signal Amplification. For the detection of protein targets in solution using the molecular biosensor assay (FIG. 1) a restriction-enzyme digestion based signal amplification methodology (FIG. 11) has recently been developed that could allow ~100 fold signal amplification compatible with the homogenous nature of the assay. This amplification approach is based on target-dependent restriction enzyme digestion of fluorescent DNA construct (S3, FIG. 11) whose fluorescence is dramatically increased upon its cleavage. Signal amplification is derived from multiple rounds of cleavage that a single target-antibody complex can catalyze. S3 component contains a sequence recognized by a restriction enzyme. Hinc II sequence will be used but any restriction enzyme that cleaves ds DNA but is inactive on ss DNA (like Hinc II) could be used. S3 also contains the probes attached to two complementary oligonucleotides that are in turn attached to S3 via flexible linkers. When S3 oligonucleotide is intact, the complementary oligonucleotides will be annealed (generating proximity-dependent signal such as, for example, FRET) due to the high local concentration resulting from their attachment to S3. Oligonucleotides used in S1 and S2 are designed to be sufficiently short that on their own they cannot anneal to S3 in any significant manner. In the presence of the target, S1 and S2 in a complex with the target will bind to S3 because the complex becomes effectively a bivalent binder for S3 that will have much increased S3 binding affinity compared to free S1 or S2. The oligonucleotides of S1 and S2 are designed to anneal to S3 such that a gap between the two oligonucleotides hybridized to S3 is exactly at the position where Hinc II would normally cleave the bottom strand of DNA duplex. Thus, when Hinc II is present in the sample, it will cleave S3 only when it is annealed to both S1 and S2 (i.e. when the target is present). Upon cleavage of S3, the complex will dissociate (cleavage of S3 will greatly decrease both the stability of the complex as well as it will result in dissociation of the two signaling oligonucleotides which in turn will eliminate the proximity-dependent signal). The complex of T with S1 and S2 can now associate with another molecule of S3 and such cleavage and dissociation cycle could be repeated many times producing signal amplification. We propose that the same events as those illustrated in FIG. 11 for a protein target in solution could be produced by the antibodies associating with the surface of the bacteria cell (as illustrated in FIG. 2). The applicability of the signal amplification scheme illustrated in FIG. 11 will be tested for detecting bacteria by preparing bacteria-specific antibodies labeled with oligonucleotides complementary to S3. A mixture of such antibodies will be incubated with various amounts of target and negative control cells in the presence of Hinc II followed by fluorescence intensity measurement. The performance of the assays employing this amplification scheme will be compared to assays employing standard FRET detection.

Example 12

Solid-Surface Based Variant of the Biosensor

Figure 12:
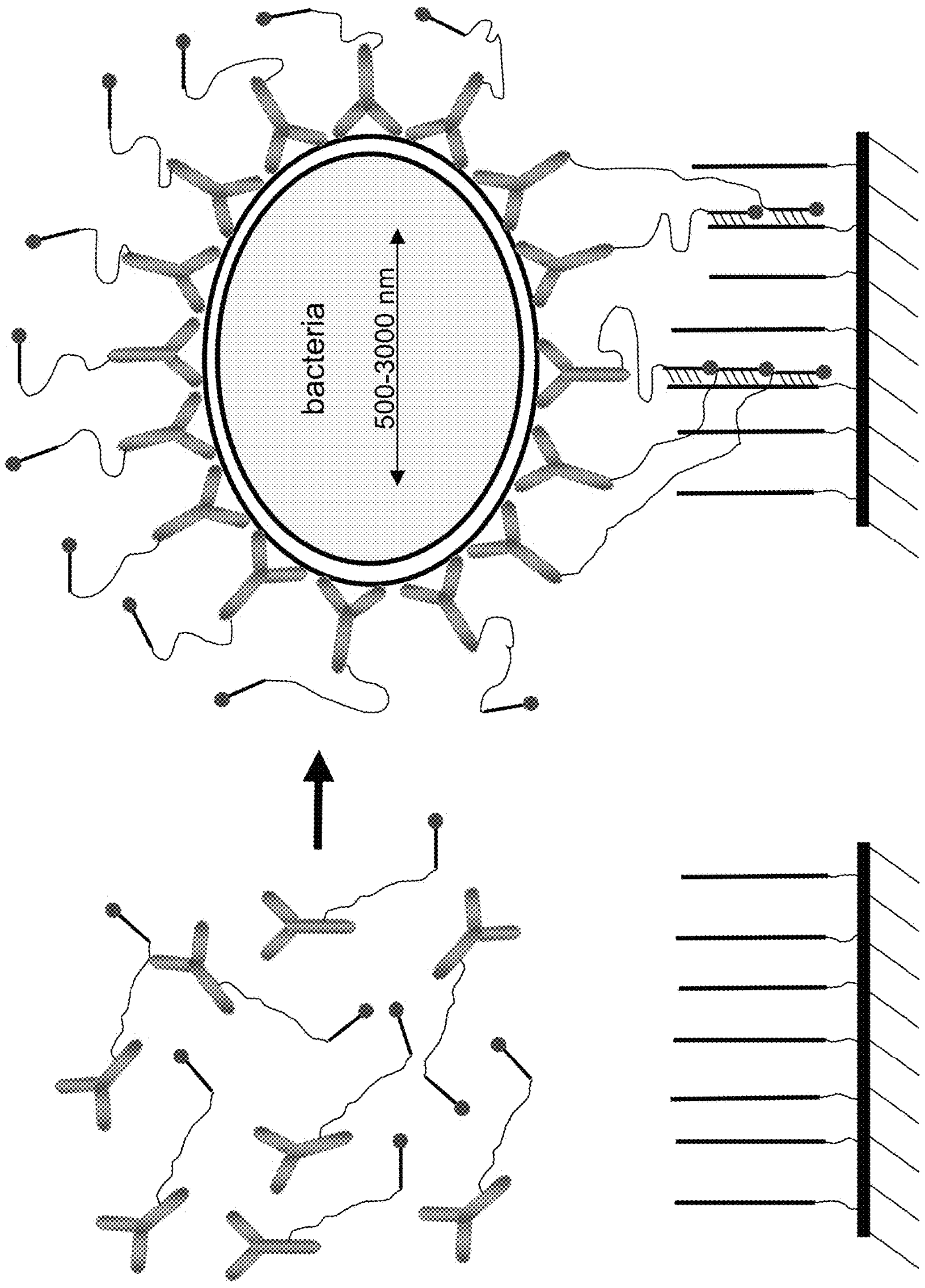
FIG. 12 depicts a design of the solid-surface variant of the sensor for detecting bacteria. Oligonucleotide containing multiple copies of a sequence complementary to the signaling oligonucleotide used for labeling the antibody is immobilized on the solid surface.
Figure 13:
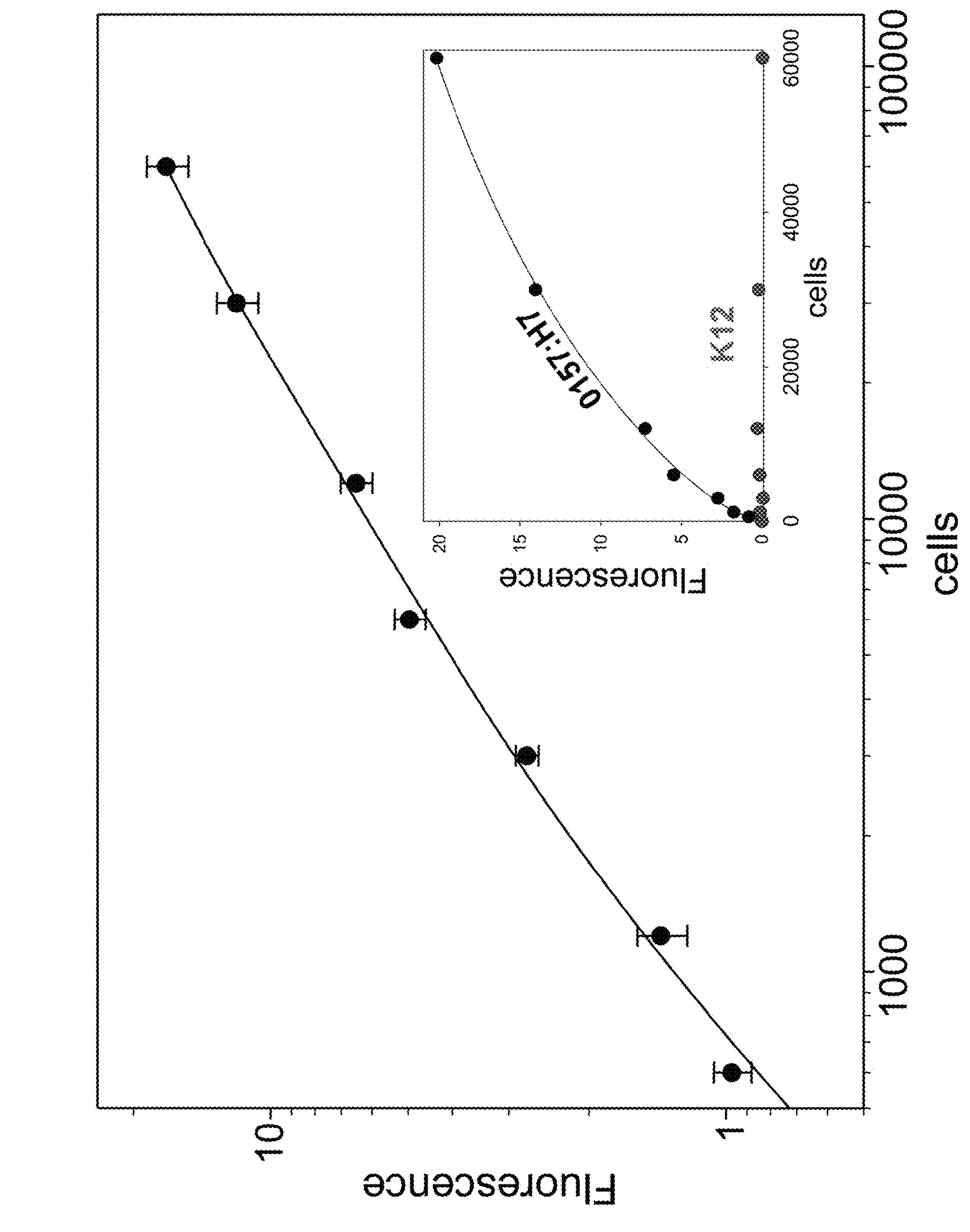
FIG. 13 depicts a proof-of-principle validation of the design illustrated in FIG. 12. Various amounts of *E. coli* 0157:H7 cells were incubated in the presence of 20 nM antibody conjugated to fluorescein-modified signaling oligonucleotide in microplate wells containing immobilized complementary oligonucleotide. After washing the wells with the buffer the fluorescence remaining in the wells were read on a plate reader. Inset: Specificity of the solid-surface based sensor. No signal in the presence of *E. coli* K12 was detected (red symbols).

The goal of this example will be to develop an alternative design of the sensor illustrated in FIG. 12. While implementing this sensor design will require a more sophisticated instrumentation, its potential advantages include an increase in sensitivity and the possibility for multiplexed simultaneous detection of several targets. In this design, an antibody modified with a single short oligonucleotide via a long flexible linker will be used (FIG. 12). The second oligonucleotide containing a segment(s) complementary to this oligonucleotide will be immobilized on a solid surface. The oligonucleotide that will be used to label the antibody will be designed to provide some affinity for binding to the immobilized complementary oligonucleotide but this affinity will be set (affinity of the interaction between two oligonucleotides can be set at any desired level using length and the sequence of oligonucleotides as a variable) to be low enough that at nanomolar concentrations of the antibody very little association of the free antibodies with the immobilized oligonucleotide will be observed (for example, a KD in mM range would fulfill this design requirement). We hypothesize that when the target cells are added, the antibodies bound to the surface of the cell will in effect create a multivalent particle capable of multivalent interactions with the immobilized oligonucleotides (FIG. 12). Due to the multivalent character of these interactions, the target cells should bind to the solid surface with very high affinity. We suggest that this binding of the target cells to the solid surface induced by the association of the labeled antibody with the cell surface antigens can be utilized for effective detection of the target cells. FIG. 13 illustrates a feasibility experiment demonstrating detection of target bacteria with the solid-surface assay according to a design illustrated in FIG. 12.

Since the antibodies are labeled with fluorescence probes, any fluorescence detection specific to surface-bound fluorescent probes could be potentially used for the readout of the signal. The performance of two variants of this alternative assay design will be investigated. In the first variant, oligonucleotide complementary to the antibody-bound oligonucleotide will be immobilized in the well of a 96-well microplate. The sample will be incubated with oligonucleotide-labeled antibody followed by washing the wells with the buffer and readout of fluorescence remaining in the well. Second variant will involve a real-time readout of the association of the target cell-antibody complex with the solid surface using Total Internal Reflection Fluorescence (TIRF). This mode of signal readout will involve more technically complex instrumentation but will likely be more sensitive and faster. Additionally, it would be possible to immobilize oligonucleotides of unique sequences at different areas (spots) of TIRF slide. This would allow a simultaneous multiplexed detection of several target cells by using antibodies specific to each of the target cell labeled with a unique sequence oligonucleotide complementary to oligonucleotide immobilized at a unique spot of the slide.

Most of the parameters of the optimal homogenous assay to be determined in above will be also applicable to the solid surface-based assay. However, the optimal length of the oligonucleotides attached to the antibody in the case of the assay illustrated in FIG. 12 is likely to be different than in the homogenous assay (FIG. 2). It is likely that lower affinity oligonucleotides may be required for optimal performance in the case of solid-surface based assay. The performance of the solid-surface variant of the assay (FIG. 12) will therefore be tested utilizing the oligonucleotides with hybridization ΔG's in the range from 5 to 8 kcal/mole. In these experiments, oligonucleotides complementary to the antibody-bound oligonucleotides will be immobilized in the well of a 96-well microplate. This version of the solid-surface based assay is relatively easy to set up and perform and the conclusions regarding the optimal length of the complementary oligonucleotides obtained with this assay variant should be also applicable to the real-time TIRF-based assay. Streptavidin-coated plates and biotinylated oligonucleotide will be used to immobilize the oligonucleotides on a surface of the microplate well. For each oligonucleotide length tested, various amounts of target cells and in parallel, negative control cells, will be incubated in the wells of the microplate coated with the corresponding complementary oligonucleotide. The wells will be washed three times with the buffer and fluorescence remaining in each well will be measured on Analyst AD microplate reader (Molecular Devices, Sunnyvale, Calif.). Sensitivity of detection and signal-to-background ratio for each oligonucleotide length tested will be used to determine the optimal length of the oligonucleotide.

Immobilized oligonucleotides containing multiple repeats of the sequence complementary to the oligonucleotide used to label the antibody will also be tested (as opposed to a single copy of such sequence as depicted in FIG. 12). The affinity of the target cell coated with oligonucleotide-labeled antibodies for binding to the solid-surface containing oligonucleotides with multiple repeats of the complementary sequence may be greatly improved which would be beneficial for the performance of solid-surface based assay.

Example 13

TIRF Detection

Figure 14:
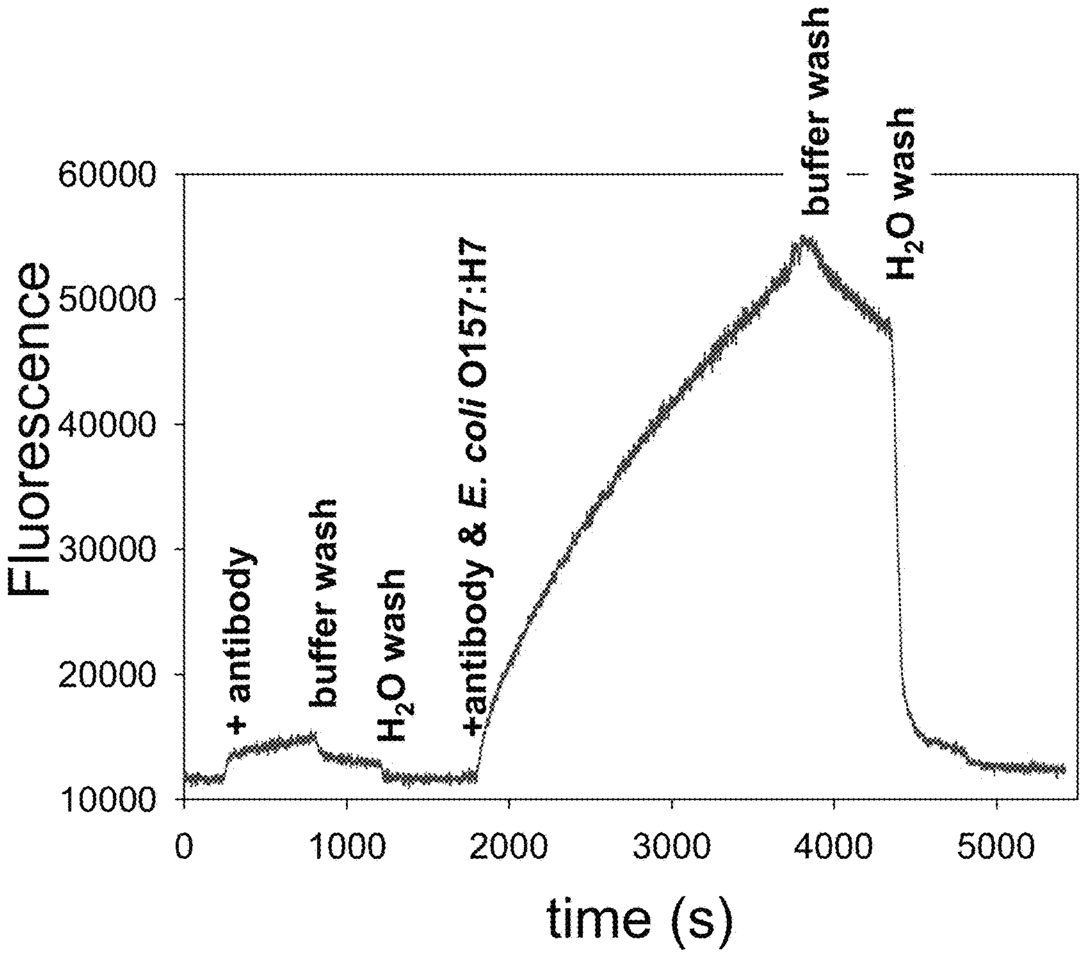
FIG. 14 depicts a proof-of-principle for a TIRF-based solid-surface based biosensor for bacteria. Oligonucleotide containing multiple copies of a sequence complementary to the signaling oligonucleotide used for labeling the antibody was immobilized on the surface of a quartz slide. TIRF-induced fluorescence originating from the surface of the slide was monitored. Only a small signal was observed upon injecting the sample containing only labeled antibody whereas large signal was observed in the presence of target bacteria.
Figure 15A:
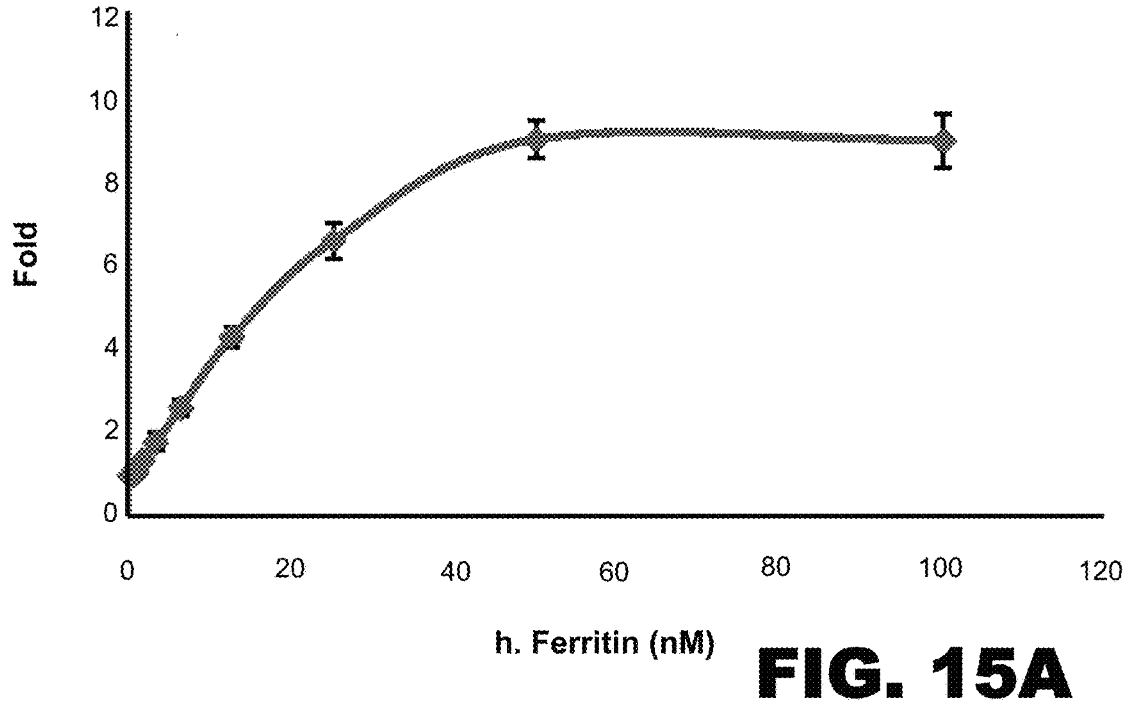
FIG. 15A-B depicts two standard curves for a ferritin assay.
Figure 15B:
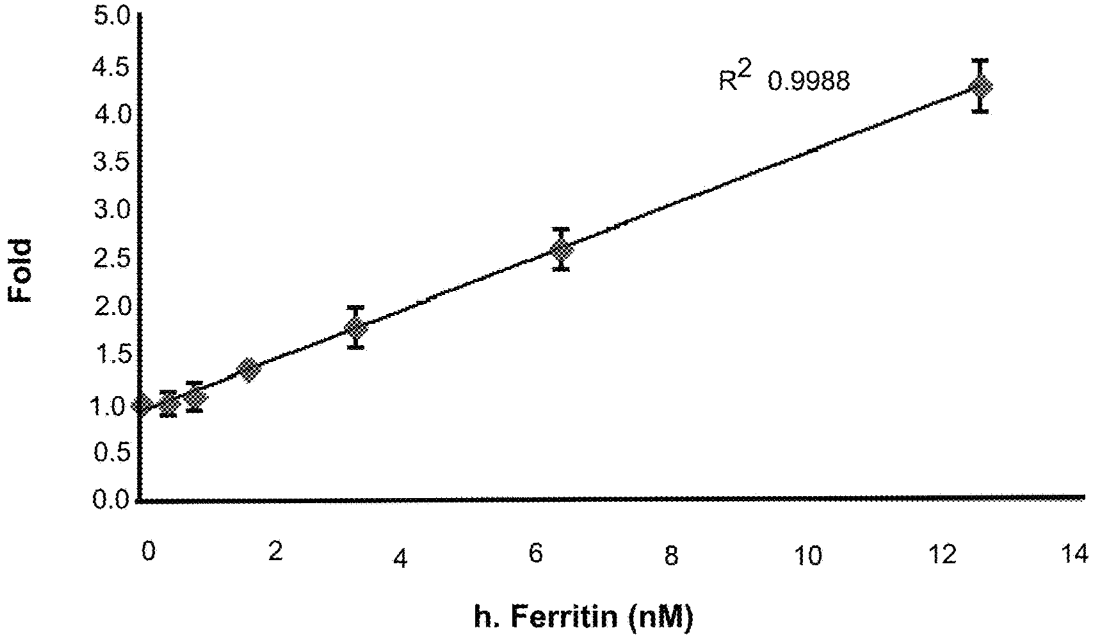

TIRF (Total Internal Reflection Fluorescence) [31-34] uses evanescent wave generated near the surface of the glass slide by a light beam reflected from the slide to limit excitation to the molecules bound to slide surface. Limiting the excitation only to molecules bound to the slide surface allows real-time monitoring of the interactions of labeled molecules with the slide surface since the fluorescent molecules in the bulk solution are not excited and do not contribute to the signal. Also, limiting excitation to a very thin (few hundred nanometers typically) layer of the sample reduces background, increasing the sensitivity of detection. This allows the detection of fluorescence even from single molecules [31, 34]. TIRF can be thus adopted for real-time detection of target cell induced association of the antibody-coated cell to the slide surface coated with the oligonucleotides complementary to the oligonucleotide used to label the antibody. Real-time detection capability will allow rapid readout time and the outstanding signal detection sensitivity of TIRF can produce significant sensitivity gains. FIG. 14 illustrates the feasibility of experiments demonstrating detection of target bacteria with the solid-surface assay implementing TIRF detection.

Additionally, TIRF-based detection offers a unique potential of developing a multiplexed assay that will allow simultaneous detection of multiple target cells. To test this, four oligonucleotides of unique sequence will be immobilized to four distinct areas ("spots") on the TIRF slide. The antibodies for the four targets will be labeled, each with a unique sequence oligonucleotide complementary to the oligonucleotide immobilized in one of the spots. When a sample containing the target cells mixed with the oligonucleotide-labeled antibodies for the four targets will be introduced to the TIRF slide, the presence of a specific target cell will be detected by the appearance of the fluorescence signal at the spot containing an immobilized oligonucleotide of the sequence complementary to the oligonucleotide used to label the antibody for this target. To test this multiplexed TIRF-based assay, samples containing only one of the targets at a time will be tested to verify that fluorescence signal will be detected only at a correct spot. Samples containing mixtures of target cells at various proportions will then be added to test the ability of the multiplexed assay to correctly report the composition of these complex samples.

Example 14

Biosensor Design for Detecting Viruses

As in the case of pathogenic bacteria, rapid detection and identification of viruses is an essential element of infectious disease diagnosis, treatment and prevention. For example, rapid detection of avian flu infection in poultry is critical to controlling outbreaks. Virus particles, while much smaller then bacterial cells (for example, influenza virus is 80-120 nm in diameter), should be still large enough to produce FRET signal resulting from co-binding of many labeled antibodies to surface epitopes of the virus according to scheme in FIG. 2. Influenza A and B viruses will be used as model targets to investigate the applicability of our sensors for detecting viruses. The gamma-radiation inactivated viruses and the virus-specific antibodies will be purchased from BiosPacific (Emeryville, Calif.).

If the results of experiments described above show the general feasibility of applying sensor design illustrated in FIG. 2 for virus detection, the performance of the solid-surface based assay will be tested for detecting viruses. Both the microplate-based assay and TIRF-based assay will be evaluated. These data will be used to determine sensitivity, specificity and reproducibility (CV's) of the optimized assays. These parameters will be used to evaluate the feasibility of employing the solid-surface based assays for detecting viruses.

Example 15

Detection of a Protein Comprising a Repeating Epitope

An anti-human Ferritin antibody was converted into a molecular biosensor pair (anti-human Ferritin-A2-AA2-FAM and anti-human Ferritin-A2-AM-Oyster). These two molecular pincers were mixed as a 2× assay mixture (40 nM of each pincer, calculated as oligo concentration) in TBS with 0.1 mg/ml BSA. The purified human Ferrintin protein standard was diluted in 10 μl TBS with 0.1 mg/ml BSA range from 200 nM to OnM. 10 μl of the 2× assay solution was added to 10 μl of each sample. The plate was incubated at RT for 40 min and the FRET (485 nm/665 nm) and FAM (485 nm/535 nm) was recorded on a TECAN plate reader. The relative fluorescence fold change (RF) was calculated from raw fluorescence values using the following formula where RF=Relative fluorescence fold change, $FRET_S$=FRET signal of the sample, $FRET_0$=FRET signal of the black, $FRET_B$=background FRET signal (buffer alone), $FAM_S$=FAM signal of the sample, $FAM_0$=FAM signal of the blank, $FAM_B$=background FAM signal (buffer alone).

$$RF=(FRET_S-FRET_S)(FAM_0-FAM_S)/(FRET_0-FRET_S)(FAM_S-FAM_B)$$

What is claimed is:

1. A method for detecting a target comprising at least one repeating epitope, the method comprising contacting a sample comprising the target with a molecular biosensor, the biosensor comprising:

$R^{24}$—$R^{25}$—$R^{26}$—$R^{27}$, $R^{28}$—$R^{29}$—$R^{30}$—$R^{31}$, and

O wherein:

$R^{24}$ is a peptide epitope binding agent that binds to a repeating epitope on a target antibody;

$R^{25}$ is a flexible linker attaching $R^{24}$ to $R^{26}$;

$R^{26}$ and $R^{30}$ are a pair of nucleotide sequences that are not complementary to each other, but are complementary to two distinct regions on O;

$R^{27}$ and $R^{31}$ together comprise a detection means such that when $R^{26}$ and $R^{30}$ associate with O a detectable signal is produced;

$R^{28}$ is a peptide epitope binding agent that binds to the same repeating epitope on the target antibody as $R^{24}$;

$R^{29}$ is a flexible linker attaching $R^{28}$ to $R^{30}$; and

O is a nucleotide sequence comprising a first region that is complementary to $R^{26}$, and a second region that is complementary to $R^{30}$, and detecting the signal produced by the association of $R^{26}$ with O and $R^{30}$ with O, wherein the signal indicates the presence of the target antibody.

2. The method of claim 1, wherein the detection means is selected from the group consisting of FRET, fluorescence cross-correlation spectroscopy, fluorescence quenching, fluorescence polarization, flow cytometry, scintillation proximity, luminesense resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

3. The method of claim 1, wherein 80% of the maximum signal may be detected at 5 minutes.

4. The method of claim 1, wherein O comprises formula (IV):

$R^{32}$—$R^{33}$—$R^{34}$—$R^{35}$—$R^{36}$ (IV)

wherein:

$R^{32}$, $R^{34}$, and $R^{36}$ are nucleotide sequences not complementary to any of $R^{26}$, $R^{30}$, $R^{33}$, or $R^{35}$;

$R^{33}$ is a nucleotide sequence complementary to $R^{26}$;

$R^{35}$ is a nucleotide sequence that is complementary to $R^{30}$;

$R^{33}$ is not adjacent to $R^{35}$; and wherein $R^{32}$, $R^{34}$, and $R^{36}$ are from 2 to 20 nucleotides in length; and $R^{33}$ and $R^{35}$ comprise a length such that the free energy of association between $R^{33}$ and $R^{26}$ and $R^{35}$ and $R^{30}$ is from −5 to −12 kcal/mole at a temperature from 21° C. to 40° C. and at a salt concentration from 1 mM to 100 mM.

5. The method of claim 1, wherein $R^{25}$ and $R^{29}$ are from 50 to 250 angstroms in length and are independently selected from the group consisting of a heterobifunctional chemical linker, a homobifunctional chemical linker, polyethylene glycol, and nucleic acid.

6. The method of claim 1, wherein $R^{26}$ and $R^{30}$ are from 2 to 20 nucleotides in length.

7. A method for detecting a target in a sample, the method comprising:

(a) contacting a surface comprising an immobilized oligonucleotide construct 0, with two epitope binding agents constructs, and a sample, the epitope binding agents constructs comprising:

$R^{24}$—$R^{25}$—$R^{26}$—$R^{27}$;

$R^{28}$—$R^{29}$—$R^{30}$—$R^{31}$;

wherein:

$R^{24}$ is a peptide epitope binding agent that binds to a repeating epitope on a target antibody;

$R^{25}$ is a flexible linker attaching $R^{24}$ to $R^{26}$;

$R^{26}$ and $R^{30}$ are a pair of nucleotide sequences that are not complementary to each other, but are complementary to two distinct regions on O;

$R^{27}$ and $R^{31}$ are labels that together comprise a detection means such that when $R^{26}$ and $R^{30}$ associate with O a detectable signal is produced;

$R^{28}$ is a peptide epitope binding agent that binds to the same repeating epitope on the target antibody as $R^{24}$;

$R^{29}$ is a flexible linker attaching $R^{28}$ to $R^{30}$; and

O is a nucleotide sequence comprising a first region that is complementary to $R^{26}$, and a second region that is complementary to $R^{30}$, wherein O is immobilized to the surface irrespective of the association between $R^{26}$ and O or $R^{30}$ and O; and (b) detecting whether $R^{26}$ and $R^{30}$ bind to O, wherein the binding indicates that the target antibody is present in the sample.

* * * * *